(12) United States Patent
Friesen et al.

(10) Patent No.: US 8,815,294 B2
(45) Date of Patent: *Aug. 26, 2014

(54) PHARMACEUTICAL COMPOSITIONS OF DEXTRAN POLYMER DERIVATIVES AND A CARRIER MATERIAL

(75) Inventors: Dwayne T. Friesen, Bend, OR (US); David T. Vodak, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/223,207

(22) Filed: Aug. 31, 2011

(65) Prior Publication Data

US 2012/0058196 A1   Mar. 8, 2012

Related U.S. Application Data

(60) Provisional application No. 61/380,102, filed on Sep. 3, 2010.

(51) Int. Cl.
*A61K 9/14* (2006.01)
*A61K 31/721* (2006.01)

(52) U.S. Cl.
USPC .......................................... 424/489; 424/493

(58) Field of Classification Search
CPC ...... A61K 31/721; A61K 9/51; A61K 5/5161
USPC .......................................... 514/59; 424/489
See application file for complete search history.

(56) References Cited

U.S. PATENT DOCUMENTS

| | | | |
|---|---|---|---|
| 4,451,452 A | 5/1984 | Deibig et al. |
| 4,501,726 A | 2/1985 | Schroder et al. |
| 4,615,881 A | 10/1986 | Deibig et al. |
| 4,713,249 A | 12/1987 | Schröder |
| 5,688,931 A | 11/1997 | Nogusa et al. |
| 5,744,153 A | 4/1998 | Yewey et al. |
| 5,759,563 A | 6/1998 | Yewey et al. |
| 5,780,044 A | 7/1998 | Yewey et al. |
| 5,792,475 A | 8/1998 | Davis et al. |
| 5,928,669 A | 7/1999 | Davis et al. |
| 5,981,719 A | 11/1999 | Woiszwillo et al. |
| 6,048,515 A | 4/2000 | Kresse et al. |
| 6,090,925 A | 7/2000 | Woiszwillo et al. |
| 6,165,506 A | 12/2000 | Jain et al. |
| RE37,053 E | 2/2001 | Hanes et al. |
| 6,200,590 B1 | 3/2001 | Eley |
| 6,268,053 B1 | 7/2001 | Woiszwillo et al. |
| 6,303,148 B1 | 10/2001 | Hennink et al. |
| 6,395,302 B1 | 5/2002 | Hennink et al. |
| 6,497,903 B1 | 12/2002 | Hennink et al. |
| 6,541,039 B1 | 4/2003 | Lesniak et al. |
| 6,576,221 B1 | 6/2003 | Kresse et al. |
| 6,589,557 B2 | 7/2003 | Straub et al. |
| 6,589,562 B1 | 7/2003 | Shefer et al. |
| 6,610,317 B2 | 8/2003 | Straub et al. |
| 6,632,671 B2 | 10/2003 | Unger |
| 6,685,927 B2 | 2/2004 | Sumian et al. |
| 6,740,310 B2 | 5/2004 | Edwards et al. |
| 6,740,631 B2 | 5/2004 | Shefer et al. |
| 6,800,297 B2 | 10/2004 | Altreuter et al. |
| 6,825,161 B2 | 11/2004 | Shefer et al. |
| 6,835,389 B1 | 12/2004 | Dohi et al. |
| 6,887,493 B2 | 5/2005 | Shefer et al. |
| 6,932,983 B1 | 8/2005 | Straub et al. |
| 6,942,868 B2 | 9/2005 | Edwards et al. |
| 6,977,087 B2 | 12/2005 | Edwards et al. |
| 6,979,466 B2 | 12/2005 | Lesniak et al. |
| 6,998,393 B2 | 2/2006 | Jin et al. |
| 7,018,657 B2 | 3/2006 | Dickinson et al. |
| 7,060,296 B2 | 6/2006 | Hennink et al. |
| 7,078,057 B2 | 7/2006 | Kerkhof |
| 7,087,246 B2 | 8/2006 | Kim et al. |
| 7,163,700 B2 | 1/2007 | Bogue |
| 7,300,919 B2 | 11/2007 | Patton |
| 7,378,110 B2 | 5/2008 | Truong-Le et al. |
| 7,468,151 B2 | 12/2008 | van Buitenen et al. |
| 7,521,069 B2 | 4/2009 | Patton et al. |
| 7,541,022 B2 | 6/2009 | Staniforth et al. |
| 7,625,865 B2 | 12/2009 | Colombo et al. |
| 7,928,089 B2 | 4/2011 | Morton et al. |
| 2002/0076443 A1 | 6/2002 | Stein et al. |
| 2002/0141943 A1 | 10/2002 | Kresse et al. |
| 2003/0026843 A1 | 2/2003 | Bogue |
| 2003/0054037 A1 | 3/2003 | Babcock et al. |
| 2003/0118514 A1 | 6/2003 | Larhrib et al. |
| 2003/0166509 A1 | 9/2003 | Edwards et al. |

(Continued)

FOREIGN PATENT DOCUMENTS

| | | |
|---|---|---|
| DE | 4136324 | 5/1993 |
| DE | 4208946 | 9/1993 |
| EP | 0051707 | 5/1982 |
| EP | 0053580 | 6/1982 |
| EP | 0842657 | 5/1998 |
| EP | 0910412 | 4/1999 |
| EP | 0914832 | 5/1999 |
| EP | 0941068 | 9/1999 |
| EP | 1184032 | 3/2002 |
| EP | 1239844 | 9/2002 |

(Continued)

OTHER PUBLICATIONS

Cruz et al., "Peptide synthesis containing a B-cell and a T-cell epitope on dextran beads and evaluation of humoral response against bead-peptide construct," *Letters in Peptide Science*, vol. 7, No. 4, pp. 229-237 (Jul. 2000).

(Continued)

*Primary Examiner* — Gina C Justice

(74) *Attorney, Agent, or Firm* — Klarquist Sparkman, LLP

(57) ABSTRACT

Pharmaceutical compositions are provided comprising (a) nanoparticles of an active agent and a dextran polymer derivative, and (b) a carrier material.

7 Claims, No Drawings

(56) References Cited

U.S. PATENT DOCUMENTS

| | | |
|---|---|---|
| 2003/0207776 A1 | 11/2003 | Shefer et al. |
| 2004/0062778 A1 | 4/2004 | Shefer et al. |
| 2004/0091535 A1 | 5/2004 | Vachon et al. |
| 2004/0105821 A1 | 6/2004 | Bernstein et al. |
| 2004/0109894 A1 | 6/2004 | Shefer et al. |
| 2004/0137071 A1 | 7/2004 | Unger |
| 2004/0176391 A1 | 9/2004 | Weers et al. |
| 2004/0184995 A1 | 9/2004 | Katsuma et al. |
| 2004/0191186 A1 | 9/2004 | Edwards et al. |
| 2004/0224019 A1 | 11/2004 | Shefer et al. |
| 2004/0234597 A1 | 11/2004 | Shefer et al. |
| 2005/0019270 A1 | 1/2005 | Finlay et al. |
| 2005/0058710 A1 | 3/2005 | Straub et al. |
| 2005/0065047 A1 | 3/2005 | Shefer et al. |
| 2005/0112235 A1 | 5/2005 | Shefer et al. |
| 2005/0158249 A1 | 7/2005 | Edwards et al. |
| 2005/0181059 A1 | 8/2005 | Jacob et al. |
| 2005/0191246 A1 | 9/2005 | Bechtold-Peters et al. |
| 2005/0238716 A1 | 10/2005 | Verrijk et al. |
| 2005/0250881 A1 | 11/2005 | Gref et al. |
| 2006/0025355 A1 | 2/2006 | Duddu et al. |
| 2006/0039985 A1 | 2/2006 | Bennett et al. |
| 2006/0093557 A1 | 5/2006 | Dickinson et al. |
| 2006/0110462 A1 | 5/2006 | Papadopoulos et al. |
| 2006/0121121 A1 | 6/2006 | Jin et al. |
| 2006/0127480 A1 | 6/2006 | Tobyn et al. |
| 2006/0141029 A1 | 6/2006 | Heller et al. |
| 2006/0141047 A1 | 6/2006 | Heller et al. |
| 2006/0141075 A1 | 6/2006 | Talbott |
| 2006/0159625 A1 | 7/2006 | Tarara et al. |
| 2006/0165785 A1 | 7/2006 | Noga et al. |
| 2006/0204582 A1 | 9/2006 | Stein et al. |
| 2006/0210640 A1 | 9/2006 | Kerkhof |
| 2006/0246142 A1 | 11/2006 | Liversidge et al. |
| 2006/0257491 A1 | 11/2006 | Morton et al. |
| 2006/0280691 A1 | 12/2006 | Wang et al. |
| 2006/0292081 A1 | 12/2006 | Morton et al. |
| 2007/0003615 A1 | 1/2007 | Jenkins et al. |
| 2007/0003628 A1 | 1/2007 | Liversidge et al. |
| 2007/0015719 A1 | 1/2007 | Jenkins et al. |
| 2007/0031490 A1 | 2/2007 | Loebenberg et al. |
| 2007/0042049 A1 | 2/2007 | Liversidge et al. |
| 2007/0043030 A1 | 2/2007 | Morton et al. |
| 2007/0104792 A1 | 5/2007 | Jenkins |
| 2007/0134339 A1 | 6/2007 | Jenkins et al. |
| 2007/0134341 A1 | 6/2007 | Kipp et al. |
| 2007/0148100 A1 | 6/2007 | Jenkins |
| 2007/0148236 A1 | 6/2007 | Babcock et al. |
| 2007/0178051 A1 | 8/2007 | Pruitt et al. |
| 2007/0189979 A1 | 8/2007 | Zeng et al. |
| 2008/0057003 A1 | 3/2008 | Bechtold-Peters et al. |
| 2008/0152585 A1 | 6/2008 | Ryde et al. |
| 2008/0213370 A1* | 9/2008 | Desai et al. .......... 424/486 |
| 2008/0213374 A1 | 9/2008 | Carty et al. |
| 2008/0220074 A1 | 9/2008 | Bosch et al. |
| 2008/0234227 A1 | 9/2008 | Soula et al. |
| 2008/0241267 A1 | 10/2008 | Verrijk |
| 2008/0292707 A1 | 11/2008 | Babcock et al. |
| 2009/0011031 A1 | 1/2009 | Staniforth et al. |
| 2009/0038612 A1 | 2/2009 | Nilsson et al. |
| 2009/0047336 A1 | 2/2009 | Yang et al. |
| 2009/0181100 A1 | 7/2009 | Bosch et al. |
| 2009/0202628 A1* | 8/2009 | Sung et al. .......... 424/451 |
| 2009/0238867 A1 | 9/2009 | Jenkins et al. |
| 2009/0269396 A1 | 10/2009 | Cipolla et al. |
| 2009/0269411 A1 | 10/2009 | Bellinghausen et al. |
| 2009/0270308 A1 | 10/2009 | Libin et al. |
| 2009/0274765 A1 | 11/2009 | Beduneau et al. |
| 2009/0285905 A1 | 11/2009 | Gordon et al. |
| 2010/0081956 A1 | 4/2010 | Hyde et al. |
| 2011/0033550 A1* | 2/2011 | Kalombo .......... 424/499 |
| 2012/0003282 A1 | 1/2012 | Miller et al. |

FOREIGN PATENT DOCUMENTS

| | | |
|---|---|---|
| EP | 1255534 | 11/2002 |
| EP | 1371364 | 12/2003 |
| EP | 1393718 | 3/2004 |
| EP | 1741424 | 1/2007 |
| KR | 2009058420 A * | 6/2009 |
| WO | WO94/02122 | 2/1994 |
| WO | WO96/04017 | 2/1996 |
| WO | WO97/44013 | 11/1997 |
| WO | WO98/00170 | 1/1998 |
| WO | WO98/22093 | 5/1998 |
| WO | WO98/31346 | 7/1998 |
| WO | WO98/58673 | 12/1998 |
| WO | WO00/13672 | 3/2000 |
| WO | WO00/72827 | 12/2000 |
| WO | WO01/45674 | 6/2001 |
| WO | WO01/45677 | 6/2001 |
| WO | WO01/60339 | 8/2001 |
| WO | WO01/78689 | 10/2001 |
| WO | WO01/95877 | 12/2001 |
| WO | WO01/97865 | 12/2001 |
| WO | WO02/00207 | 1/2002 |
| WO | WO02/17884 | 3/2002 |
| WO | WO02/45575 | 6/2002 |
| WO | WO02/083154 | 10/2002 |
| WO | WO03/030872 | 4/2003 |
| WO | WO03/043586 | 5/2003 |
| WO | WO03/092659 | 11/2003 |
| WO | WO03/105780 | 12/2003 |
| WO | WO2004/006897 | 1/2004 |
| WO | WO2004/012690 | 2/2004 |
| WO | WO2004/019908 | 3/2004 |
| WO | WO2004/030659 | 4/2004 |
| WO | WO2004/041991 | 5/2004 |
| WO | WO2004/060351 | 7/2004 |
| WO | WO2004/082660 | 9/2004 |
| WO | WO2004/112695 | 12/2004 |
| WO | WO2004/112696 | 12/2004 |
| WO | WO2005/007080 | 1/2005 |
| WO | WO2005/025541 | 3/2005 |
| WO | WO2005/025550 | 3/2005 |
| WO | WO2005/032511 | 4/2005 |
| WO | WO2005/055976 | 6/2005 |
| WO | WO2005/084644 | 9/2005 |
| WO | WO2005/115330 | 12/2005 |
| WO | WO2006/002140 | 1/2006 |
| WO | WO2006/003504 | 1/2006 |
| WO | WO2006/036617 | 4/2006 |
| WO | WO2006/130943 | 12/2006 |
| WO | WO2007/064912 | 6/2007 |
| WO | WO2007/146943 | 12/2007 |
| WO | WO2008/038111 | 4/2008 |
| WO | WO2008/070538 | 6/2008 |
| WO | WO2008/092057 | 7/2008 |
| WO | WO2008/137960 | 11/2008 |
| WO | WO2008/151022 | 12/2008 |
| WO | WO2009/046440 | 4/2009 |
| WO | WO2010/009146 | 1/2010 |
| WO | WO2010/102065 | 9/2010 |
| WO | WO2010/102066 | 9/2010 |
| WO | WO2010/132827 | 11/2010 |
| WO | WO2010/146406 | 12/2010 |
| WO | WO2010/146408 | 12/2010 |
| WO | WO2010/146409 | 12/2010 |
| WO | WO2011/057017 | 5/2011 |
| WO | WO2011/060250 | 5/2011 |

OTHER PUBLICATIONS

International Search Report and Written Opinion for PCT/US2010/056515, filed Nov. 12, 2010 (mailed Feb. 22, 2011).

US5,849,884, 12/1998, Woiszwillo et al. (withdrawn).

Grenha et al., "Microencapsulated chitosan nanoparticles for lung protein delivery," *European Journal of Pharmaceutical Sciences*, vol. 25, Issues 4-5, pp. 427-437 (Jul.-Aug. 2005).

Heinze et al., "Functional Polymers Based on Dextran," *Advances in Polymer Science*, vol. 205, pp. 199-291 (Sep. 2006).

(56) References Cited

OTHER PUBLICATIONS

Kawashima et al., "A New Powder Design Method to Improve Inhalation Efficiency of Pranlukast Hydrate Dry Powder Aerosols by Surface Modification with Hydroxypropylmethylcellulose Phthalate Nanospheres," *Pharmaceutical Research*, vol. 15, No. 11, pp. 1748-752 (Nov. 1998).

Lemarchand et al., "Influence of polysaccharide coating on the interactions of nanoparticles with biological systems," *Biomaterials*, vol. 27, Issue 1, pp. 108-118 (Jan. 2006).

Liebert et al., "Nanoparticles on the Basis of Highly Functionalized Dextrans," *Journal of the American Chemical Society*, vol. 127, No. 30, pp. 10484-10485 (Aug. 2005).

Niwa et al., "Aerosolization of Lactide/Glycolide Copolymer (PLGA) Nanospheres for Pulmonary Delivery of Peptide-drugs," *Yakugaku Zasshi Journal of the Pharmaceutical Society of Japan*, vol. 115, No. 9, pp. 732-741 (Sep. 1995).

Rasenack et al., "Micronization of Anti-Inflammatory Drugs for Pulmonary Delivery by a Controlled Crystallization Process," *Journal of Pharmaceutical Sciences*, vol. 92, No. 1, pp. 35-44 (Jan. 2003).

Sham et al., "Formulation and characterization of spray-dried powders containing nanoparticles for aerosol delivery to the lung," *International Journal of Pharmaceutics*, vol. 269, Issue 2, pp. 457-467 (Jan. 2004).

Steckel et al., "In-situ-micronization of disodium cromoglycate for pulmonary delivery," *European Journal of Pharmaceutics and Biopharmaceutics*, vol. 55, No. 2, pp. 173-180 (Mar. 2003).

Steckel et al., "In vitro characterization of jet-milled and in-situ-micronized fluticasone-17-propionate," *International Journal of Pharmaceutics*, vol. 258, Issues 1-2, pp. 65-75 (Jun. 2003).

Yamamoto et al., "Poly(lactic-co-glycolic acid) Nanosphere Composite Prepared with Mechanofusion Dry Powder Composition System for Improving Pulmonary Insulin Delivery with Dry Powder Inhalation," *Journal of Pharmaceutical Science and Technology*, Japan, vol. 64, No. 4, pp. 245-253 (Jan. 2004).

Chow et al., "Particle Engineering for Pulmonary Drug Delivery," *Pharmaceutical Research*, vol. 24, No. 3, pp. 411-437 (Mar. 2007).

Final Office action from U.S. Patent and Trademark Office for U.S. Appl. No. 13/254,802, mailed Aug. 6, 2013.

Final Office action from U.S. Patent and Trademark Office for U.S. Appl. No. 13/259,082, mailed Nov. 7, 2013.

Hornig et al., "Nanoscale structures of dextran esters," *Carbohydrate Polymers*, vol. 68, Issue 2, pp. 280-286 (Mar. 2007).

International Search Report and Written Opinion for PCT/US2011/040222, filed Jun. 13, 2011 (mailed Dec. 6, 2011).

Office action from U.S. Patent and Trademark Office for U.S. Appl. No. 13/254,802, mailed Nov. 16, 2012.

Prado et al., "Preparation and characterization of a novel starch-based interpolyelectrolyte complex as matrix for controlled drug release," Carbohydrate Research, vol. 344, No. 11, pp. 1325-1331 (Jul. 2009).

Restriction Requirement from the U.S. Patent and Trademark Office in U.S. Appl. No. 13/254,802, dated May 29, 2012.

\* cited by examiner

PHARMACEUTICAL COMPOSITIONS OF DEXTRAN POLYMER DERIVATIVES AND A CARRIER MATERIAL

CROSS REFERENCE TO RELATED APPLICATIONS

This application claims the benefit of U.S. Provisional Application No. 61/380,102, filed Sep. 3, 2010, which is incorporated herein in its entirety by reference.

TECHNICAL FIELD

Pharmaceutical compositions are provided comprising (a) nanoparticles of an active agent and a dextran polymer derivative, and (b) a carrier material.

BACKGROUND

Pharmaceutically active agents are generally formulated as solid or liquid dosage forms for administration. Such dosage forms generally comprise the active agent combined with excipients to form materials that may be conveniently and reliably administered to a patient in need of such therapy, and following administration, the active agent is absorbed and distributed in the patient in a way that leads to good efficacy and safety.

It is known that poorly water-soluble drugs may be formulated as nanoparticles. Nanoparticles are of interest for a variety of reasons, such as to improve the bioavailability of poorly water-soluble drugs, to provide targeted drug delivery to specific areas of the body, to reduce side effects, or to reduce variability in vivo.

A variety of approaches have been taken to formulate drugs as nanoparticles. One approach is to decrease the size of crystalline drug by grinding or milling the drug in the presence of a surface modifier. Another approach to forming nanoparticles is to precipitate the drug in the presence of a film forming material such as a polymer.

There remain a number of problems associated with the use of nanoparticles to deliver pharmaceutical compounds to the body. The nanoparticles must be stabilized so that they do not aggregate into larger particles in aqueous suspensions. Often surface modifiers such as surfactants are used to stabilize the nanoparticles, but such materials can have adverse physiological effects when administered in vivo. In addition, without a surface modifier present, the surface of the nanoparticles is unprotected, leading to a decrease in performance and stability.

In addition, it is often desirable to formulate nanoparticles as a dry material to improve patient compliance and facilitate incorporating the nanoparticles into a suitable dosage form. However, when liquids are removed from suspensions of nanoparticles, the nanoparticles often agglomerate or aggregate. When the resulting dry material is then administered to an aqueous solution (either in vitro or in vivo), large particles are formed, corresponding to the agglomerated or aggregated nanoparticles. These aggregates or agglomerated particles reduce the performance of the formulation.

Accordingly, there is a continuing need for nanoparticles that are stable, in the sense of not aggregating into larger particles, and that improve the bioavailability of active agents.

SUMMARY OF INVENTION

A pharmaceutical composition comprises (a) nanoparticles comprising an active agent and a dextran polymer derivative, and (b) a carrier material. The nanoparticles have an average size of less than 1000 nm. The carrier material constitutes from 5 wt % to 99 wt % of the combined mass of (1) said nanoparticles and (2) said carrier material. The dextran polymer derivative is selected from dextran acetate, dextran propionate, dextran succinate, dextran acetate propionate, dextran acetate succinate, dextran propionate succinate, dextran acetate propionate succinate, and mixtures thereof.

In one embodiment, the carrier material is selected from synthetic polymers, polysaccharides, derivatized polysaccharides, sugars, sugar alcohols, organic acids, salts of organic acids, inorganic salts, proteins, amino acids, phospholipids, and pharmaceutically acceptable forms, derivatives, and mixtures thereof.

In one embodiment, the carrier material is selected from polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic)acid, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), ethyl cellulose, cellulose acetate, cellulose butyrate, cellulose acetate butyrate, trehalose, glucose, sucrose, raffinose, lactose, mannitol, erythritol, xylitol, polydextrose, oleic acid, citric acid, tartaric acid, edetic acid, malic acid, sodium citrate, sodium bicarbonate, albumin, gelatin, acacia, casein, caseinate, glycine, leucine, serine, alanine, isoleucine, tri-leucine, lecithin, phosphatidylcholine, and pharmaceutically acceptable forms, derivatives, and mixtures thereof.

In another embodiment, the carrier material is selected from lactose, mannitol, trehalose, sucrose, citric acid, sodium citrate, leucine, glycine, dextran, and pharmaceutically acceptable forms, derivatives, and mixtures thereof.

In one embodiment, the nanoparticles comprise from 0.01 to 99 wt % of an active agent and from 1 to 99.99 wt % of a dextran polymer derivative. In another embodiment, the active agent and the dextran polymer derivative constitute at least 75 wt % of the nanoparticles. In still another embodiment, the active agent and the dextran polymer derivative constitute at least 90 wt % of the nanoparticles. In yet another embodiment, the nanoparticles consist essentially of the active agent and the dextran polymer derivative.

In one embodiment, the dextran polymer derivative is selected from dextran succinate, dextran acetate succinate, dextran propionate succinate, dextran acetate propionate succinate, and mixtures thereof. In another embodiment, the dextran polymer derivative is selected from dextran acetate succinate, dextran propionate succinate, dextran acetate propionate succinate, and mixtures thereof.

In one embodiment, the dextran polymer derivative has a degree of substitution (DS) for acetate substituents of 0 to 2.8, a DS for propionate substituents of 0 to 2.8, and a DS for succinate substituents of 0 to 2.8. In another embodiment, the dextran polymer derivative has a degree of substitution for succinate of at least 0.05.

In one embodiment, the dextran polymer derivative has a molecular weight ranging from 3000 daltons to 100,000 daltons. In another embodiment, the dextran polymer derivative has a molecular weight ranging from 3000 daltons to 70,000 daltons.

In one embodiment, the composition is formulated for inhalation, and the dextran polymer derivative is at least one of aqueous soluble and enteric.

In one embodiment, the dextran polymer derivative is dextran acetate. In another embodiment, the dextran polymer derivative is dextran propionate. In another embodiment, the dextran polymer derivative is dextran succinate. In yet another embodiment, the dextran polymer derivative is dextran acetate propionate. In another embodiment, the dextran polymer derivative is dextran acetate succinate. In another embodiment, the dextran polymer derivative is dextran propionate succinate. In still another embodiment, the dextran polymer derivative is dextran acetate propionate succinate.

In one embodiment, the composition is administered to an animal via a mode selected from oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

In one embodiment, the composition comprises a plurality of particles having a mass median aerodynamic diameter of 0.5 to 100 μm for inhalation. In another embodiment, the composition comprises a plurality of particles having a mass median aerodynamic diameter of 10 to 100 μm for inhalation, wherein a weight fraction of particles having a mass median aerodynamic diameter of less than 10 μm is less than 0.1. In yet another embodiment, the composition comprises a plurality of particles having a mass median aerodynamic diameter of 0.5 to 10 μm for delivering an active agent to lower airways, wherein a weight fraction of particles having a mass median aerodynamic diameter of greater than 10 μm is less than 0.1.

Disclosed embodiments of the pharmaceutical composition provide one or more of the following advantages. Because the pharmaceutical composition comprises (a) nanoparticles comprising an active agent and a dextran polymer derivative, and (b) a carrier material, when added to an aqueous solution the composition rapidly forms a nanoparticle suspension.

The dextran polymer derivatives have a combination of substituent degrees of substitution tailored to provide utility for nanoparticle compositions.

When used to form combinations of active agents, such polymers provide enhanced concentrations of dissolved active agent in a use environment. When used in combination with active agents that are prone to rapid crystallization from supersaturated aqueous solutions, such polymers are particularly effective at sustaining high concentrations of the active agent and thereby enhancing absorption of active agent in vivo. The compositions also provide a more stable composition.

The foregoing and other objectives, features, and advantages of the invention will be more readily understood upon consideration of the following detailed description of the invention.

DETAILED DESCRIPTION OF PREFERRED EMBODIMENTS

Pharmaceutical compositions are provided comprising (a) nanoparticles comprising an active agent and a dextran polymer derivative, and (b) a carrier material. Dextran polymer derivatives, active agents, nanoparticles and methods for making them, carrier materials, suitable compositions and methods for making them, and suitable methods for delivering the compositions to a patient in need of therapy are described in detail below.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Dextran Polymer Derivatives

Dextran polymer derivatives are polymers formed by the derivatization of dextran with ester-linked groups. The groups ester-linked to the dextran may be acetate, propionate, succinate, or any combination of the three groups. Dextran is an α-D-1,6-glucose-linked glucan. It may have side-chains linked to the backbone of the dextran polymer, with the degree of branching being approximately 5%, and the branches being mostly 1-2 glucose units long. A fragment of the dextran structure is illustrated below.

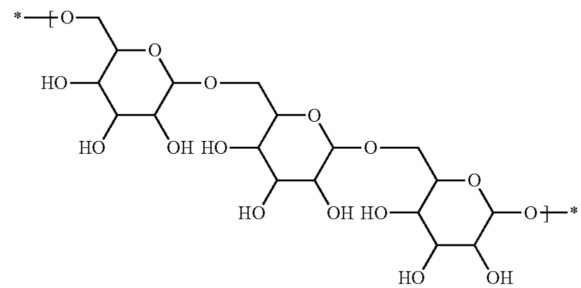

The term "dextran polymer derivative" refers to any of the family of dextran polymers that have acetate, propionate, and/or succinate groups attached via ester linkages to a significant fraction of the dextran polymer's hydroxyl groups.

In one embodiment, the dextran polymer derivative is selected from dextran acetate, dextran propionate, dextran succinate, dextran acetate propionate, dextran acetate succinate, dextran propionate succinate, dextran acetate propionate succinate, and mixtures thereof. In another embodiment, the dextran polymer derivative is selected from dextran acetate succinate, dextran propionate succinate, dextran acetate propionate succinate, and mixtures thereof. In another embodiment, the dextran polymer derivative is dextran acetate succinate. In yet another embodiment, the dextran polymer derivative is dextran propionate succinate.

For example, a fragment of dextran propionate succinate is illustrated below.

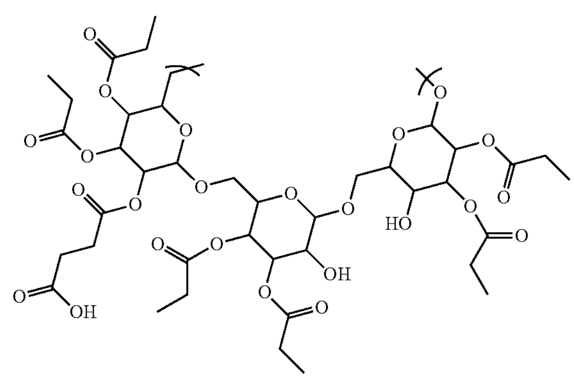

The degree of substitution of each substituent is chosen so that the active agent combined with the dextran polymer derivative will be suitable for the intended formulation.

"Degree of substitution" or "DS" refers to the average number of the three hydroxyls per saccharide repeat unit on the dextran chain that have been substituted. For example, if all of the hydroxyls on the dextran chain have been substituted by acetate groups, the degree of substitution of acetate groups is 3. In the structure of dextran propionate succinate shown above, the degree of substitution of propionate groups is 2, while the degree of substitution of succinate groups is 0.33.

In one embodiment, the degree of substitution of the acetate, propionate, and succinate groups are such that when adding the total degree of substitution of acetate, propionate and succinate, the total degree of substitution is greater than or equal to 0.05. In another embodiment, the total degree of substitution is greater than or equal to 0.15. In another embodiment, the total degree of substitution is greater than or equal to 0.25. In still another embodiment, the total degree of substitution is greater than or equal to 0.50. In yet another embodiment, the total degree of substitution is greater than or equal to 0.75.

In one embodiment, the dextran polymer derivative has the following degree of substitution (DS) for acetate, propionate, and succinate substituents: $DS_{acetate}$ ranges from 0 to 2.8, $DS_{propionate}$ ranges from 0 to 2.8, and $DS_{succinate}$ ranges from 0 to 2.8. In another embodiment, the degree of substitution for succinate is at least 0.05.

In one embodiment, the dextran polymer derivative is dextran acetate, wherein the degree of substitution for acetate groups ranges from 0.05 to 3.0. In another embodiment, the dextran polymer derivative is dextran acetate, wherein the degree of substitution for acetate groups ranges from 0.05 to 2.0. In another embodiment, the dextran polymer derivative is dextran acetate, wherein the degree of substitution for acetate groups ranges from 0.25 to 1.8. In another embodiment, the dextran polymer derivative is dextran acetate, wherein the degree of substitution for acetate groups is greater than 1.0.

In still another embodiment, the dextran polymer derivative is dextran propionate, wherein the degree of substitution for propionate groups ranges from 0.05 to 3.0. In another embodiment, the dextran polymer derivative is dextran propionate, wherein the degree of substitution for propionate groups ranges from 0.05 to 2.0. In another embodiment, the dextran polymer derivative is dextran propionate, wherein the degree of substitution for propionate groups ranges from 0.25 to 2.0. In another embodiment, the dextran polymer derivative is dextran propionate, wherein the degree of substitution for propionate groups ranges from 0.5 to 2.0. In another embodiment, the dextran polymer derivative is dextran propionate, wherein the degree of substitution for propionate groups is greater than 1.0.

In still another embodiment, the dextran polymer derivative is dextran succinate, wherein the degree of substitution for succinate groups ranges from 0.05 to 3.0. In another embodiment, the dextran polymer derivative is dextran succinate, wherein the degree of substitution for succinate groups ranges from 0.05 to 2.8. In another embodiment, the dextran polymer derivative is dextran succinate, wherein the degree of substitution for succinate groups ranges from 0.5 to 2.5.

In another embodiment, the dextran polymer derivative is dextran acetate propionate, wherein the degree of substitution for acetate groups ranges from 0.05 to 2.5, and the degree of substitution for propionate groups ranges from 0.05 to 2.5. In another embodiment, the dextran polymer derivative is dextran acetate propionate, wherein the degree of substitution for acetate groups ranges from 0.1 to 2.0, and the degree of substitution for propionate groups ranges from 0.1 to 2.0.

In another embodiment, the dextran polymer derivative is dextran acetate succinate, wherein the degree of substitution for acetate groups ranges from 0.25 to 2.5, and the degree of substitution for succinate groups ranges from 0.05 to 1.5. In another embodiment, the dextran polymer derivative is dextran acetate succinate, wherein the degree of substitution for acetate groups ranges from 0.5 to 2.5, and the degree of substitution for succinate groups ranges from 0.05 to 1.5. In still another embodiment, the dextran polymer derivative is dextran acetate succinate, wherein the degree of substitution for acetate groups ranges from 1.0 to 2.3, and the degree of substitution for succinate groups ranges from 0.1 to 1.5.

In another embodiment, the dextran polymer derivative is dextran propionate succinate, wherein the degree of substitution for propionate groups ranges from 0.1 to 2.5, and the degree of substitution for succinate groups ranges from 0.05 to 1.5. In another embodiment, the dextran polymer derivative is dextran propionate succinate, wherein the degree of substitution for propionate groups ranges from 0.25 to 2.0, and the degree of substitution for succinate groups ranges from 0.1 to 1.5.

In another embodiment, the dextran polymer derivative is dextran acetate propionate succinate, wherein the degree of substitution for acetate groups ranges from 0.05 to 2.5, the degree of substitution for propionate groups ranges from 0.05 to 2.5, and the degree of substitution for succinate groups ranges from 0.05 to 1.5. In another embodiment, the dextran polymer derivative is dextran acetate propionate succinate, wherein the degree of substitution for acetate groups ranges from 0.1 to 2.0, the degree of substitution for propionate groups ranges from 0.1 to 2.0, and the degree of substitution for succinate groups ranges from 0.1 to 1.5.

In one embodiment, the dextran polymer derivative has a degree of substitution of succinate that is 0.05 or more. A degree of substitution of succinate groups of 0.05 or more is desirable as this imparts a negative charge to the polymer at physiologically relevant pH ranges (pH 1-8). When making nanoparticles comprising the active agent and a dextran polymer derivative with a $DS_{succinate} \geq 0.05$, this charge serves to stabilize the nanoparticles in aqueous solution, minimizing or avoiding aggregation. Finally, the presence of succinate groups allows the dextran polymer derivative to be relatively hydrophobic in its protonated form for dissolution in organic solvents; for physical stability, resulting in low water absorption; and for compatibility with hydrophobic active agents. In one embodiment, a dextran polymer derivative with a $DS_{succinate} \geq 0.05$ is water soluble or dispersible when ionized, as it is in pH environments above about pH 5 (e.g., in vivo).

In one embodiment, the dextran used to form the dextran polymer derivative has a molecular weight that may range from 1,000 to 200,000 daltons. As used herein, by "molecular weight" is meant the number-average molecular weight as determined by chromatographic methods well known in the art. In these methods, the number-average molecular weight corresponds to the arithmetic mean of the molecular weights of individual macromolecules. In one embodiment, the dextran used to form the dextran polymer derivative has a molecular weight of from 1,000 to 200,000 daltons. In another embodiment, the dextran used to form the dextran polymer derivative has a molecular weight of from 2,000 to 70,000 daltons. In still another embodiment, the dextran used to form the dextran polymer derivative has a molecular weight of from 2,000 to 25,000 daltons.

Thus, in one embodiment, the dextran polymer derivative has a molecular weight of from 1,000 to 200,000 daltons. In another embodiment, the dextran polymer derivative has a molecular weight ranging from 3,000 daltons to 100,000 daltons. In another embodiment, the dextran polymer derivative has a molecular weight of from 3,000 to 70,000 daltons. In still another embodiment, the dextran polymer derivative has a molecular weight of from 2,000 to 25,000 daltons.

The degree of substitution of the substituents may be chosen such that the polymer has the desired physical properties. In one embodiment, the degree of substitution is adjusted to obtain a dextran polymer derivative with the desired aqueous solubility or dispersability. A test to determine the aqueous solubility of a dextran polymer derivative may be performed as follows. The dextran polymer derivative is initially present in bulk powder form with an average particle size of greater than about 1 micron. The polymer alone is administered at a concentration of 0.2 mg/mL to a buffer solution at the desired pH and stirred for approximately 1 hour at room temperature. Next, a nylon 0.45 μm filter is weighed, and the solution is filtered. The filter is then dried overnight at 40° C., and weighed the next day. The aqueous solubility of the polymer is calculated from the amount of polymer added to the buffer solution minus the amount of polymer remaining on the filter.

Similar procedures can be used to determine the effect of pH on the aqueous solubility of the dextran polymer derivatives. In this case the procedures are performed using aqueous buffer solutions with various pH values.

In one embodiment, the dextran polymer derivative is aqueous soluble. By "aqueous soluble" is meant that the dextran polymer derivative has an aqueous solubility of at least 1 mg/mL over at least a portion of the physiologically relevant pH range of 1-8. When the dextran polymer derivative is dextran acetate, the $DS_{acetate}$ should be less than 1.5. When the dextran polymer derivative is dextran propionate, the $DS_{propionate}$ should be less than 1.3. When the dextran polymer derivative is dextran acetate propionate, the combined degree of substitution of acetate and propionate should be less than 1.5, with the combined degree of substitution lower as the percentage of propionate relative to acetate increases. When the dextran polymer derivative also includes a $DS_{succinate}$ of ≥0.05, somewhat higher degrees of substitution of acetate and propionate can be tolerated with the polymer being aqueous soluble. Generally, increasing the degree of substitution of succinate also promotes solubility of the dextran polymer derivative at pH values above 5.0.

In another embodiment, the degree of substitution on the dextran polymer derivative is chosen so that the dextran polymer derivative is an enteric polymer. By "enteric polymer" is meant that the polymer has an aqueous solubility of less than 0.1 mg/mL at a pH of 3.0 or less, and an aqueous solubility of at least 1 mg/mL at a pH of greater than 7. The actual pH above which it is desired for the dextran polymer derivative to become aqueous soluble will depend on the application and can be varied by adjusting the ratio of the acetate plus propionate groups to the succinate groups. The pH value where the polymer becomes soluble will generally increase from 3 to a 7 as the ratio of acetate plus propionate groups to succinate groups increases.

In still another embodiment, the degree of substitution on the dextran polymer derivative is chosen so that the dextran polymer derivative is poorly aqueous soluble. By "poorly aqueous soluble" is meant that the polymer has a solubility of less than 0.1 mg/mL over at least a portion of the physiologically relevant pH range of 1-8. Generally, for a dextran polymer derivative to be poorly aqueous soluble, the combined degree of substitution of acetate and propionate is high (greater than 1), while the degree of substitution of succinate is low (less than 0.1).

The degree of substitution of substituents may also be used to form dextran polymer derivatives with other desirable properties, depending on the formulation desired. For example, in some embodiments, it is desirable that the absorption of water by the polymer be low, such as for powders for pulmonary delivery of the composition. A relatively high degree of substitution of any of the acetate, propionate, or succinate groups or combinations thereof will result in a dextran polymer derivative that absorbs less water from the surrounding atmosphere relative to compositions formed from underivatized dextran. In some embodiments, this leads to increased stability of the active agent in the composition. In particular, when the composition is a powder, low absorption of water can lead to the Tg of the composition being higher and therefore the powder being resistant to agglomeration (e.g., for respirable particles) and, when the composition is a solid dispersion, the active agent will tend to remain dispersed and not separate from the polymer as amorphous or crystalline active agent domains.

Thus, in one embodiment, the degree of substitution of acetate, propionate, and succinate are chosen such that the mass of water absorbed by the dextran polymer derivative is significantly less than that absorbed by underivatized dextran. In one embodiment, the mass of water absorbed by the dextran polymer derivative is at least 10% less than that absorbed by underivatized dextran when measured by dynamic vapor absorption at 90% relative humidity (RH) and 25° C. For comparison, the mass of water absorbed by underivatized dextran, when measured by dynamic vapor absorption at 90% RH and 25° C. is about 26 wt %. Thus, in one embodiment, the dextran polymer derivative absorbs less than 23 wt % water when measured by dynamic vapor absorption at 90% RH at 25° C. In another embodiment, the dextran polymer derivative absorbs less than 20 wt % water at 90% RH at 25° C. In still another embodiment, the dextran polymer derivative absorbs less than 18 wt % water at 90% RH at 25° C.

The addition of ester-linked acetate, propionate, and succinate groups to the dextran polymer to reduce water absorption also results in the glass-transition temperature (Tg) of the polymer equilibrated with a humid atmosphere being higher than that of the corresponding underivatized dextran. This higher Tg is desirable for some compositions comprising an active agent and dextran polymer derivative, for example, for long-term stability of compositions comprising non-crystalline active agent.

Thus, in one embodiment, the degree of substitution of acetate, propionate, and succinate is chosen such that the Tg of the dextran polymer derivative is significantly higher than that of underivatized dextran when exposed to a humid atmosphere. In one embodiment, the Tg of the dextran polymer derivative is at least 10° C. greater than that of underivatized dextran when the powders are exposed to a 50% RH atmosphere at 25° C. For comparison, the Tg of underivatized dextran powder when exposed to a 50% RH atmosphere at 25° C. is about 45 to 50° C. Thus, in one embodiment, the Tg of the dextran polymer derivative is at least 50° C. when exposed to a 50% RH atmosphere at 25° C. In another embodiment, Tg of the dextran polymer derivative is at least 60° C. when exposed to a 50% RH atmosphere at 25° C.

In one embodiment, the dextran polymer derivative is biocompatible. By "biocompatible" is meant that for some delivery routes, the polymer is compatible with and has no significant toxic effect on the living organism to which it is administered. In one embodiment, the polymer does not significantly elicit humoral or cell-based immune responses when administered in vivo.

In yet another embodiment, the dextran polymer derivative is biodegradable. By "biodegradable" is meant that the polymer will degrade when administered in vivo. By "degrade" is meant that in an in vivo use environment, the polymer is broken down into smaller species that can be absorbed, metabolized, or otherwise eliminated or "cleared" from the use environment. This degradation can occur through enzymatic, hydrolytic, oxidative, or other reaction, as is well known in the art. The polymer may also degrade into aqueous soluble species that can be cleared from the in vivo use environment. For example, the degradation products may be renally cleared through the kidneys or may enter the lymphatic system and then exit through the gastro-intestinal tract.

Synthesis of Dextran Polymer Derivatives

Methods for preparation of ester derivatives of carbohydrates are known. See for example Advances in Polymer Science, 205, *Polysaccharides II*, Edited by Dieter Klemm (Springer-Verlag, Berlin Heidelberg, 2006). Methods for the preparation of the dextran polymer derivatives of the present invention can be derived from such known methods. Specifically, the dextran polymer derivatives can be prepared as follows. In a first method, dextran is first modified by substitution with an alkyl group followed by addition of succinate. The dextran is first dissolved in a suitable solvent system such as formamide, dimethyl formamide (DMF), or N-methylpyrrolidone (NMP), together with a base, such as pyridine or the sodium salt of the carboxylate corresponding to the alkyl group to be substituted. An anhydride of the alkyl group to be substituted onto the dextran backbone is then added to the mixture. The reaction mixture is then stirred at temperatures ranging from 0 to 100° C. for a period of from about 30 minutes to 72 hours. When the resulting dextran polymer derivative is poorly aqueous soluble, the reaction can then be quenched by adding water to precipitate the polymer. The resulting precipitate can be collected by filtration. Alternatively, the polymer can be isolated by extraction into a solvent, such as ethyl acetate or methylene chloride, and the extraction solvent removed, for example, by evaporation or spray drying. The polymer can be further rinsed, filtered and dried prior to use.

The resulting dextran polymer derivative is then dissolved in the carboxylic acid corresponding to the alkyl group that has been substituted together with the sodium salt of the corresponding carboxylate. For example, if dextran propionate has been prepared, then it is dissolved in propionic acid together with sodium propionate. Succinic anhydride is then added. The reaction mixture may then be stirred at temperatures ranging from 0 to 100° C. for a period of from about 30 minutes to 72 hours. The reaction may then be quenched by adding water to precipitate the polymer. The resulting precipitate may be collected by filtration. Alternatively, the polymer may be isolated by extraction into a solvent, such as ethyl acetate or methylene chloride, and the extraction solvent removed, for example, by evaporation or spray drying. The polymer may be further rinsed, filtered and dried prior to use.

In another method, dextran is first modified by substitution with an alkyl group followed by addition of succinate, but the dextran alkyl ester is not isolated and purified prior to addition of the succinic anhydride. In this method, the dextran alkyl ester is first formed, followed by addition of succinic anhydride.

In yet another method, the dextran is modified by substitution with an alkyl group and succinate simultaneously. In this method, dextran may be first dissolved in a suitable solvent system such as formamide, DMF, or NMP, together with the sodium salt of the carboxylate corresponding to the alkyl group to be substituted. An anhydride of the alkyl group to be substituted onto the dextran backbone and succinic anhydride may then be added to the mixture. The reaction mixture may then be stirred at temperatures ranging from 0 to 100° C. for a period of from about 30 minutes to 72 hours. The reaction may then be quenched by adding water to precipitate the polymer. The resulting precipitate may be collected by filtration. Alternatively, the polymer may be isolated by extraction into a solvent, such as ethyl acetate or methylene chloride, and the extraction solvent removed, for example, by evaporation or spray drying. The polymer may be further rinsed, filtered and dried prior to use.

The degree of substitution of alkyl esters and succinate groups on the dextran polymer may be determined using standard techniques, such as nuclear magnetic resonance (NMR) analysis or high-performance liquid chromatography (HPLC). For example, $^{13}C$ NMR analysis may be used to determine the number of alkyl ester and succinate groups using the ratio of the peak area of the groups to the peak area of the anomeric carbon in the dextran ring.

Active Agents

Compositions containing dextran polymer derivatives are suitable for use with any biologically active compound desired to be administered to a patient in need of the active agent. The compositions may contain one or more active agents. As used herein, by "active agent" is meant a drug, medicament, pharmaceutical, therapeutic agent, nutraceutical, or other compound that may be desired to be administered to the body. The active agent may be a "small molecule," generally having a molecular weight of 2000 Daltons or less. The active agent may also be a "biological active agent." Biological active agents include proteins, antibodies, antibody fragments, peptides, oligonucleotides, vaccines, and various derivatives of such materials. In one embodiment, the active agent is a small molecule. In another embodiment, the active agent is a biological active agent. In still another embodiment, the active agent is a mixture of a small molecule and a biological active agent.

The active agent may be highly water soluble (i.e., greater than 100 mg/mL), sparingly water soluble (i.e., 5-30 mg/mL), or poorly water soluble (i.e., less than 5 mg/mL). In one embodiment, the active agent is "poorly water soluble," and the active agent has a solubility in water (over the pH range of 6.5 to 7.5 at 25° C.) of less than 5 mg/mL. The active agent may have an even lower aqueous solubility, such as less than 1 mg/mL, less than 0.1 mg/mL, and even less than 0.01 mg/mL.

The active agent should be understood to include the non-ionized form of the active agent, pharmaceutically acceptable salts of the active agent, or any other pharmaceutically acceptable forms of the active agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Examples of classes of active agents include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, bronchodilators, glucocorticoids, steroids, and antiviral agents.

Nanoparticles Comprising

An Active Agent and Dextran Polymer Derivatives

The compositions of the present invention comprise nanoparticles comprising the active agent and the dextran polymer derivative. By "nanoparticles" is meant a plurality of small particles in which the average size of the particles is less than 1000 nm. In suspension, by "average size" is meant the effective cumulant diameter as measured by dynamic light scattering (DLS), using for example, Brookhaven Instruments' 90Plus particle sizing instrument. By "size" is meant the diameter if the particles were spherical particles, or the maximum diameter for non-spherical particles. In some embodiments, the average size of the nanoparticles is less than 750 nm, less than 500 nm, less than 400 nm, less than 300 nm, less than 200 nm, and even less than 150 nm. In one embodiment, the average size of the nanoparticles is less than 150 nm. In another embodiment, the average size of the nanoparticles is less than 100 nm. In still another embodiment, the average size of the nanoparticles is less than 75 nm. In yet another embodiment, the average size of the nanoparticles is less than 50 nm. In another embodiment, the nanoparticles range in size from 1 nm to 1000 nm, 1 nm to 750 nm, 1 nm to 500 nm, 1 nm to 400 nm, from 1 nm to 300 nm, from 1 nm to 200 nm, from 10 nm to 1000 nm, from 30 nm to 1000 nm, from 10 nm to 500 nm, or from 30 nm to 500 nm.

The width of the particle size distribution in suspension is given by the "polydispersity" of the particles, which is defined as the relative variance in the correlation decay rate distribution, as is known by one skilled in the art. See B. J. Fisken, "Revisiting the method of cumulants for the analysis of dynamic light-scattering data," Applied Optics, 40(24), 4087-4091 (2001) for a discussion of cumulant diameter and polydispersity. In one embodiment, the polydispersity of the nanoparticles is less than 0.5. In another embodiment, the polydispersity of the nanoparticles is less than 0.3. In one embodiment, the average size of the nanoparticles is less than 1000 nm with a polydispersity of 0.5 or less. In another embodiment, the average size of the nanoparticles is less than 750 nm with a polydispersity of 0.5 or less. In another embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 200 nm with a polydispersity of 0.5 or less. In yet another embodiment, the average size of the nanoparticles is less than 200 nm with a polydispersity of 0.3 or less.

The nanoparticles can exist in a number of different configurations. In one embodiment, the nanoparticles comprise a core, the core comprising the active agent and the dextran polymer derivative. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, Fourier transform infra red (FTIR) analysis, and Raman spectroscopy; (3) chromatographic techniques, such as high performance liquid chromatography (HPLC), and gel-permeation chromatography (GPC); and (4) other techniques known in the art.

The active agent present in the core can exist in pure active agent domains (crystalline or non-crystalline), as a thermodynamically stable solid solution of non-crystalline active agent distributed throughout the dextran polymer derivative, as a supersaturated solid solution of non-crystalline active agent distributed throughout the dextran polymer derivative, or any combination of these states or those states that lie between them. When the glass-transition temperature (Tg) of the non-crystalline active agent is different from the Tg of the pure polymer by at least 20° C., the core may exhibit a Tg that is different from the Tg of pure non-crystalline active agent or pure polymer. In one embodiment, less than 20 wt % of the active agent is present in non-crystalline active agent domains, with the remaining active agent distributed throughout the polymer.

In one embodiment, the nanoparticles are homogeneous, meaning that the composition on the surface of the nanoparticle is essentially the same as in the core of the nanoparticle. In such cases, the nanoparticles may comprise, in one embodiment, a solid amorphous dispersion of the type described in the previous section, except for the small size— less than 1000 nm. In another embodiment, the active agent is present as one or more amorphous or crystalline domains throughout each nanoparticle.

In still another embodiment, the core comprises the active agent and the dextran polymer derivative, with a surface stabilizer adsorbed to the surface portion of the nanoparticle.

In one embodiment, at least 50 wt % of the active agent in the nanoparticles is crystalline. In another embodiment, at least 75 wt % of the active agent in the nanoparticles is crystalline.

In still another embodiment, at least 90 wt % of the active agent in the nanoparticles is non-crystalline. In another embodiment, at least 95 wt % of the active agent in the nanoparticle is non-crystalline; in other words, the amount of active agent in crystalline form does not exceed 5 wt %.

Amounts of crystalline active agent may be measured by Powder X-Ray Diffraction (PXRD), by Differential Scanning calorimetry (DSC), by solid state nuclear magnetic resonance (NMR), or by any other known quantitative measurement.

The active agent and polymer are collectively present in the nanoparticle in an amount ranging from 50 wt % to 100 wt %. In one embodiment, the active agent and polymer collectively may constitute at least 60 wt %, at least 75 wt %, at least 80 wt %, or even at least 90 wt % of the nanoparticle. In another embodiment, the nanoparticles consist essentially of the active agent and the dextran polymer derivative. By "consist essentially of" is meant that the nanoparticle contains less than 1 wt % of any other excipients and that any such excipients have substantially no effect on the performance or properties of the nanoparticle.

The amount of active agent in the nanoparticle may range from 0.01 wt % to 99 wt %. In one embodiment, the amount of active agent in the nanoparticle ranges from 0.1 wt % to 80 wt %, or from 0.1 to 60 wt %, or from 1 to 40 wt %. In still another embodiment, the amount of active agent in the nanoparticle ranges from 5 wt % to 75 wt %, from 5 wt % to 60 wt %, or from 5 wt % to 50 wt %.

To minimize the total mass of the nanoparticle, high active agent loadings are desired. However, if the amount of active agent in the nanoparticle is too high, the nanoparticle suspension becomes unstable, resulting in crystallization of the active agent in the suspension. Additionally, high amounts of active agent in the nanoparticle can lead to crystalline active agent formation when the nanoparticles are isolated from suspension in solid form. Thus, in one embodiment, the amount of active agent in the nanoparticle may be less than 90 wt %, less than 80 wt %, or even less than 75 wt % the total mass of the nanoparticle.

The amount of dextran polymer derivative may range from 1 wt % to 99.99 wt %. The physical stability of the active agent in the nanoparticle tends to improve with increasing amounts of the dextran polymer derivative. Accordingly, in one embodiment, the amount of polymer in the nanoparticle is at least 5 wt %, at least 15 wt %, at least 20 wt %, or at least 25 wt %. However, too much polymer will lead to low active agent loading in the nanoparticle. Thus, in one embodiment, the amount of polymer in the nanoparticle is 80% or less.

The mass ratio of active agent to dextran polymer derivative in the nanoparticle can range from 1:999 to 9:1 (that is, from 0.1 wt % active agent to 90 wt % active agent relative to the total mass of active agent and dextran polymer derivative in the nanoparticle). In one embodiment, the mass ratio of active agent to dextran polymer derivative ranges from 1:99 to 4:1 (that is, from 1 wt % to 80 wt % active agent relative to the total mass of active agent and dextran polymer derivative), from t 1:19 to 3:1 (that is, from 5 wt % to 75 wt %), from 1:10 to 1:5 (that is, from 9 wt % to 60 wt % active agent relative to the total mass of active agent and dextran polymer derivative in the nanoparticle). In one embodiment, the mass ratio of active agent to dextran polymer derivative is less than 9:1, less than 4:1, less than 3:1, or even less than 3:2. In other embodiments, the mass ratio of active agent to dextran polymer derivative is at least 1:999, at least 1:99, and even at least 1:10.

The nanoparticles may optionally comprise a surface stabilizer in addition to the active agent and the dextran polymer derivative. The purpose of the surface stabilizer is to reduce or prevent aggregation or flocculation of the nanoparticles in an aqueous suspension, resulting in nanoparticles with improved stability. In one embodiment, the surface stabilizer is used to stabilize the nanoparticles during the formation process. The stabilizer should be inert, in the sense that it does not chemically react with the active agent in an adverse manner, and should be pharmaceutically acceptable.

The surface stabilizer may be distributed throughout the nanoparticle, it may be in higher concentration on the surface of the nanoparticle, or any combination of these. In one embodiment, the surface stabilizer is distributed throughout the nanoparticle. In another embodiment, the surface stabilizer is at a higher concentration on the surface of the nanoparticle. When the surface stabilizer is at a higher concentration on the surface of the nanoparticle, the surface stabilizer may comprise the outer portion of the nanoparticle, while the dextran polymer derivative may be present in the core of the nanoparticle.

When an optional surface stabilizer is present, it may constitute from 0.1 wt % to 50 wt % of the total mass of the nanoparticles. Generally, lower concentrations of surface stabilizer are desired. Thus, in one embodiment, the surface stabilizer constitutes 40 wt % or less, or even 30 wt % or less of the total mass of the nanoparticles.

In one embodiment, the surface stabilizer is an amphiphilic compound, meaning that it has both hydrophobic and hydrophilic regions. In another embodiment, the surface stabilizer is a surfactant, including anionic, cationic, zwitterionic, and non-ionic surfactants. Mixtures of surface stabilizers may also be used.

In one embodiment, the surface stabilizer is a dextran polymer derivative. When the surface stabilizer is a dextran polymer derivative, it may be the same or different than the dextran polymer derivative present in the core of the nanoparticle. In one embodiment, an aqueous soluble dextran polymer derivative is used as the surface stabilizer.

Exemplary surface stabilizers include dextran polymer derivatives, casein, caseinates, dextran, polyvinyl pyrrolidone (PVP), polyoxyethylene alkyl ethers, polyoxyethylene stearates, polyoxyethylene castor oil derivatives, poly(ethylene oxide-propylene oxide) (also known as poloxamers), tragacanth, gelatin, polyethylene glycol, bile salts (such as salts of dihydroxy cholic acids, including sodium and potassium salts of cholic acid, glycocholic acid, and taurocholic acid), phospholipids (such as phosphatidyl cholines, including 1,2-diacylphosphatidylcholine also referred to as PPC or lecithin), sodium dodecylsulfate (also known as sodium lauryl sulfate), benzalkonium chloride, sorbitan esters, polyoxyethylene alkyl ethers, polyoxyethylene castor oil derivatives, polyoxyethylene sorbitan fatty acid esters (polysorbates), polyoxyethylene stearates, triethanolamine, sodium docusate, sodium stearyl fumarate, sodium cyclamate, and mixtures and pharmaceutically acceptable forms thereof.

In one embodiment, the surface stabilizer is a bile salt. The bile salt may be selected from the group sodium glycocholate and sodium taurocholate.

The nanoparticles may be formed by any process that results in formation of nanoparticles comprising active agent and a dextran polymer derivative. The active agent used to form the nanoparticles may be in a crystalline or non-crystalline form, or a mixture thereof.

One process for forming nanoparticles is an emulsification process. In this process, the active agent and dextran polymer derivative are dissolved in an organic solvent that is immiscible with an aqueous solution in which active agent and polymers are poorly soluble, forming an organic solution. Solvents suitable for forming the solution of dissolved active agent and dextran polymer derivative can be any compound or mixture of compounds in which the active agent and the polymer are mutually soluble and which is immiscible with the aqueous solution. As used herein, the term "immiscible" means that the organic solvent has a solubility in the aqueous solution of less than 10 wt %, less than 5 wt %, or even less than 3 wt %. In one embodiment, the solvent is also volatile with a boiling point of 150° C. or less. Exemplary organic solvents include methylene chloride, trichloroethylene, trichloro-trifluoroethylene, tetrachloroethane, trichloroethane, dichloroethane, dibromoethane, ethyl acetate, phenol, chloroform, toluene, xylene, ethyl-benzene, benzyl alcohol, creosol, methyl-ethyl ketone, methyl-isobutyl ketone, hexane, heptane, ether, and mixtures thereof. In one embodiment, the organic solvents are methylene chloride, ethyl acetate, benzyl alcohol, and mixtures thereof.

In one embodiment, the aqueous solution is water. The optional surface stabilizer or other components that make up the exterior portion of the nanoparticles may be dissolved in the aqueous solution. When the active is water soluble, it may be dissolved in the aqueous solution.

Once the organic solution is formed, it is then mixed with the aqueous solution and homogenized to form an emulsion of fine droplets of the water immiscible solvent distributed throughout the aqueous phase. The volume ratio of organic solution to aqueous solution used in the process will generally range from 1:100 (organic solution:aqueous solution) to 2:3

(organic solution:aqueous solution). In one embodiment, the organic solution:aqueous solution volume ratio ranges from 1:9 to 1:2 (organic solution:aqueous solution). The emulsion is generally formed by a two-step homogenization procedure. The solution of active agent, polymer and organic solvent are first mixed with the aqueous solution using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration. In one embodiment, the organic solvent is removed to a level that is acceptable according to The International Committee on Harmonization (ICH) guidelines. In another embodiment, the concentration of organic solvent in the nanoparticle suspension is less than the solubility of the organic solvent in the aqueous solution. Even lower concentrations of organic solvent are often desired. Thus, the concentration of organic solvent in the nanoparticle suspension may be less than 5 wt %, less than 3 wt %, less than 1 wt %, and even less than 0.1 wt %.

An alternative process to form the nanoparticles is a precipitation process. In this process, the dextran polymer derivative is first dissolved in an organic solvent that is miscible with an aqueous solution in which the dextran polymer derivative is poorly soluble. The resulting organic solution is mixed with the aqueous solution causing the nanoparticles to precipitate. In one embodiment, the active agent is dissolved in the aqueous solution. In another embodiment, the active agent is dissolved, along with the dextran polymer derivative, in the organic solution. Solvents suitable for forming the solution of dissolved active agent and polymer can be any compound or mixture of compounds in which the active agent and the polymer are mutually soluble and which is miscible in the aqueous solution. In one embodiment, the organic solvent is also volatile with a boiling point of 150° C. or less. Exemplary solvents include acetone, methanol, ethanol, tetrahydrofuran (THF), and DMSO. Mixtures of solvents, such as 50% methanol and 50% acetone, can also be used, so long as the active agent and polymer are sufficiently soluble to dissolve the active agent and polymer. In one embodiment, the solvents are methanol, acetone, and mixtures thereof.

The aqueous solution may be any compound or mixture of compounds in which the active agent and polymer are sufficiently insoluble so as to precipitate to form nanoparticles. In one embodiment, the aqueous solution is water. In another embodiment, the optional surface stabilizer is dissolved in the aqueous solution.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

For the precipitation process, the amount of active agent and polymer in the organic solution depends on the solubility of each in the organic solvent and the desired ratio of active agent to polymer in the resulting nanoparticles. The organic solution may comprise from 0.1 wt % to 20 wt % dissolved solids. A dissolved solids content of from 0.5 wt % to 10 wt % is usually desired.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2 (organic solution:aqueous solution). In one embodiment, the organic solution:aqueous solution volume ratio ranges from 1:20 to 1:3.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. In one embodiment, the solvent is removed to a level that is acceptable according to ICH guidelines. Thus, the concentration of solvent in the nanoparticle suspension may be less than 10 wt %, less than 5 wt %, less than 3 wt %, less than 1 wt %, and even less than 0.1 wt %.

Still another process for forming nanoparticles is through a milling process, as is known in the art. One method comprises suspending the crystalline active agent in a liquid dispersion medium and applying mechanical means in the presence of grinding media to reduce the particle size of the active agent substance to the effective average particle size. The particles can be reduced in size in the presence of a dextran polymer derivative, which acts as a surface modifier. Alternatively, the particles can be contacted with the dextran polymer derivative after attrition.

Carrier Materials

The compositions of the present invention also comprise a carrier material. By "carrier material" is meant a material that is formulated with the nanoparticles to aid in delivery of the nanoparticles to the desired location and with the desired properties. The carrier material constitutes from 5 wt % to 99 wt % of the combined mass of (1) the nanoparticles and (2) the carrier material.

In one aspect, a dry, solid composition comprises (a) a plurality of nanoparticles comprising an active agent and a dextran polymer derivative, and (b) a carrier material. As used herein, the term "dry, solid pharmaceutical composition" means that the composition is in a solid form and substantially free of liquids.

The solid pharmaceutical composition may take one of many configurations. In one embodiment, at least a portion of the nanoparticles in the solid composition are encapsulated by the carrier material. By "at least a portion of the nanoparticles are encapsulated by the carrier material" means that the carrier material encapsulates at least a portion of the plurality of nanoparticles in the composition. The carrier material may encapsulate only a portion of the nanoparticles, or may encapsulate essentially all of the nanoparticles in the composition. In one embodiment, the carrier material encapsulates essentially all of the nanoparticles in the composition.

Thus, in one embodiment, the compositions may contain a plurality of nanoparticles, at least a portion of which are encapsulated by the carrier material. Those nanoparticles not encapsulated by the carrier material are in direct contact with the carrier material.

In another embodiment, a portion of the carrier material is adsorbed to the surface portion of the nanoparticles. The remaining portion of the carrier material encapsulates the nanoparticles in the composition. In this embodiment, the carrier material may act as a surface stabilizer, stabilizing the nanoparticles during the formation process or when present in aqueous suspension, reducing or preventing aggregation or flocculation of the nanoparticles prior to forming the solid composition of the invention, or when an aqueous solution is added to the solid nanoparticle composition in order to form an aqueous suspension of the nanoparticles.

In one embodiment, the carrier material is selected from synthetic polymers, polysaccharides, derivatized polysaccharides, sugars, sugar alcohols, organic acids, salts of organic acids, inorganic salts, proteins, amino acids, phospholipids, and pharmaceutically acceptable forms, derivatives, and mixtures thereof. In another embodiment, the carrier material is selected from polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic)acid, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), ethyl cellulose, cellulose acetate, cellulose butyrate, cellulose acetate butyrate, trehalose, glucose, sucrose, raffinose, lactose, mannitol, erythritol, xylitol, polydextrose, oleic acid, citric acid, tartaric acid, edetic acid, malic acid, sodium citrate, sodium bicarbonate, albumin, gelatin, acacia, casein, caseinate, glycine, leucine, serine, alanine, isoleucine, tri-leucine, lecithin, phosphatidylcholine, and pharmaceutically acceptable forms, derivatives, and mixtures thereof. Exemplary counterions suitable for forming salt forms include sodium, potassium, ammonium, calcium, magnesium, aluminum, iron, and amines. In one embodiment, the carrier material is in a sodium salt form, potassium salt form, or ammonium salt form.

In one embodiment, the carrier material is selected from lactose, mannitol, trehalose, sucrose, citric acid, sodium citrate, leucine, glycine, dextran, and pharmaceutically acceptable forms, derivatives, and mixtures thereof. In another embodiment, the carrier material is selected from lactose, mannitol, trehalose, sucrose, citric acid, sodium citrate, leucine, glycine, and pharmaceutically acceptable forms, derivatives, and mixtures thereof.

In one embodiment, the carrier material is water soluble. By "water soluble" is meant that the carrier material has a solubility in water at 25° C. of at least 1 mg/mL. In one embodiment, the carrier material is selected from polyvinyl pyrrolidone (PVP), polyethyleneoxide (PEO), poly(vinyl pyrrolidone-co-vinyl acetate), pullulan, dextran, maltodextrin, hyaluronic acid, polysialic acid, hydroxypropyl methyl cellulose (HPMC), hydroxypropyl cellulose (HPC), dextran, trehalose, glucose, sucrose, raffinose, lactose, mannitol, erythritol, xylitol, polydextrose, citric acid, tartaric acid, malic acid, sodium citrate, sodium bicarbonate, albumin, glycine, leucine, serine, alanine, isoleucine, tri-leucine, and pharmaceutically acceptable forms, derivatives, and mixtures thereof. In another embodiment, the carrier material is selected from lactose, mannitol, trehalose, sucrose, citric acid, sodium citrate, leucine, glycine, dextran, and pharmaceutically acceptable forms, derivatives, and mixtures thereof. In another embodiment, the carrier material is selected from the group lactose, mannitol, trehalose, sucrose, citric acid, sodium citrate, leucine, glycine, and pharmaceutically acceptable salt forms, derivatives, and mixtures thereof.

In yet another embodiment, the carrier has low or no water solubility (e.g., less than 0.5 mg/mL at 25° C.). Such materials may be used to slow the release of the nanoparticles in vivo. Exemplary low-solubility carrier materials include ethyl cellulose, cellulose acetate, cellulose butyrate, cellulose acetate butyrate, polymethacrylates, polyoxyethylene alkyl ethers, polyoxyethylene castor oils, polycaprolactam, polylactic acid, polyglycolic acid, poly(lactic-glycolic)acid, lipids, and derivatives, and mixtures thereof.

The carrier material constitutes from 5 wt % to 99 wt % of the combined mass of (1) the carrier material and (2) the nanoparticles. The carrier material is present in a sufficient amount so that a solid composition forms a nanoparticle suspension when administered to an aqueous use environment. Furthermore, a sufficient amount of carrier material is present to prevent or retard agglomeration of the nanoparticles into larger particles following administration to an aqueous use environment. In one embodiment, the carrier material constitutes from 10 wt % to 75 wt % of the combined mass of (1) the carrier material and (2) the nanoparticles. In another embodiment, the carrier material constitutes from 15 wt % to 50 wt % of the combined mass of (1) the carrier material and (2) the nanoparticles. In still another embodiment, the carrier material constitutes at least 10 wt % of the combined mass of (1) the carrier material and (2) the nanoparticles. In still another embodiment, the carrier material constitutes at least 20 wt % of the combined mass of (1) the carrier material and (2) the nanoparticles. In yet another embodiment, the carrier material constitutes at least 25 wt % of the combined mass of (1) the carrier material and (2) the nanoparticles. In another embodiment, the carrier material constitutes at least 40 wt % of the combined mass of (1) the carrier material and (2) the nanoparticles. In another embodiment, the carrier material constitutes at least 50 wt % of the combined mass of (1) the carrier material and (2) the nanoparticles.

In one embodiment, the effectiveness of a carrier material may be determined using a "filter potency" test. In this test the concentration of active agent after passing a suspension of the nanoparticles through a filter is determined. The solid composition is added to an aqueous solution. The concentration of active agent in the so-formed suspension is then determined using standard techniques, such as by high-performance liquid chromatography (HPLC). Next, the suspension is filtered through a filter, and the concentration of active agent in the filtered sample is determined via standard techniques. A loss in potency after filtering a sample through a filter is an indication that the nanoparticles in the sample are larger than the filter pore size. Exemplary filters that can be used in this test include a 1-μm glass fiber filter, a 0.45-μm syringe filter, and a 0.2-μm syringe filter. One skilled in the art will understand that the pore size and material of the filter should be selected to ensure the nanoparticles are not retained on the filter. Generally, the pore size of the filter and the range of nanoparticle average diameters are given as follows:

| Filter Pore Size (μm) | Suitable Range of Nanoparticle Diameters (nm) |
|---|---|
| 1 | >250 |
| 0.45 | 150 to 300 |
| 0.2 | <200 |

In one embodiment, the concentration of active agent in the filtered sample is at least 60% the concentration of active agent in the unfiltered sample. In another embodiment, the concentration of active agent in the filtered sample is at least 70% the concentration of active agent in the unfiltered sample. In yet another embodiment, the concentration of active agent in the filtered sample is at least 80% the concentration of active agent in the unfiltered sample.

Formation of Solid Compositions

The compositions of the present invention comprise nanoparticles comprising an active agent and a dextran polymer derivative, and a carrier material. The carrier material can be formulated with the nanoparticles either during the process used to form the nanoparticles or after the nanoparticles are formed.

In one embodiment, the carrier material is formulated with the nanoparticles during the nanoparticle-formation process. In this embodiment, the carrier material may be considered to be part of the nanoparticles. For the emulsion and precipitation processes described above, the carrier material can be either added to the organic solution comprising the active agent and polymer or added to the aqueous solution. In one embodiment, the carrier material is added to the aqueous solution. Formulating the carrier material in the aqueous solution is advantageous as it allows the carrier material to help reduce or eliminate flocculation or aggregation of the nanoparticles once they are formed.

In this embodiment, once the nanoparticles are formed, the resulting mixture comprises the nanoparticles suspended in the aqueous solution, which also comprises the carrier material. In one embodiment, the carrier material is dissolved in the aqueous solution. The liquids are then removed from the aqueous solution, as discussed below, resulting in a solid composition comprising the nanoparticles and the carrier material.

In another embodiment, the carrier material is formulated with the nanoparticles in suspension after the nanoparticles have been formed. This has advantages when the process for removing the organic solvent from the nanoparticle suspension would also remove a portion of the carrier material (e.g., diafiltration). This embodiment also has advantages when processes are used to increase the concentration of nanoparticles in the suspension. Generally, in this embodiment, the carrier material is added to the suspension containing the nanoparticles. In one embodiment, the carrier material is dissolved in the aqueous suspension containing the nanoparticles. The liquids are then removed from the aqueous solution, resulting in a solid composition comprising the nanoparticles and the carrier material.

Thus, a process for forming a solid composition comprises: (a) forming an organic solution comprising an active agent and a dextran polymer derivative dissolved in an organic solvent; (b) forming an aqueous solution, wherein the active agent and the dextran polymer derivative are poorly soluble in the aqueous solution; (c) mixing the organic solution with the aqueous solution to form a first mixture; (d) removing the organic solvent from the first mixture to form a suspension comprising the nanoparticles and the aqueous solution, wherein the nanoparticles have an average size of less than 1000 nm; (e) adding a carrier material to either the aqueous solution of step (b) or to the suspension of step (d), wherein the carrier material constitutes from 5 wt % to 99 wt % of the combined mass of (1) the carrier material and (2) the nanoparticles; and (f) removing liquid from the suspension to form a solid composition comprising the nanoparticles and the carrier material.

Essentially any process that removes the liquid from the suspension may be used to form a solid composition, provided the process does not affect the properties of the nanoparticles or the carrier material. Exemplary processes include spray drying, spray coating, spray layering, lyophilization, evaporation, vacuum evaporation, and filtration. In one embodiment the process is spray drying. In another embodiment the process is lyophilization. One or more processes may be combined to remove the liquid from the suspension and yield a solid composition. For example, a portion of the liquid may be removed by filtration to concentrate the suspension, followed by spray-drying to remove most of the remaining liquids, followed by a further drying step such as tray-drying.

Following removal of the liquid, the nanoparticles and carrier material are collectively present in the resulting solid composition in an amount ranging from 60 wt % to 100 wt % of the total mass of the composition. In one embodiment, the nanoparticles and carrier material collectively constitute at least 70 wt %, at least 80 wt %, or even at least 90 wt % of the composition. In one embodiment, the composition consists essentially of the nanoparticles and the carrier material. By "consists essentially of" is meant that the composition contains less than 1 wt % of any other excipients and that any such excipients have no affect on the performance or properties of the composition. This material may then be incorporated into a dosage form containing other excipients.

Delivery Routes and Methods of Treatment

In one embodiment, the invention provides a method of administering to an animal, including humans, a composition comprising (a) nanoparticles of an active agent and a dextran polymer derivative, and (b) a carrier material, via a mode selected from the group consisting of oral, buccal, mucosal, sublingual, intravenous, intra-arterial, intramuscular, subcutaneous, intraperitoneal, intraarticular, infusion, intrathecal, intraurethral, topical, subdermal, transdermal, intranasal, inhalation, pulmonary tract, intratracheal, intraocular, ocular, intraaural, vaginal, and rectal.

In one embodiment, the composition comprising an active agent, a dextran polymer derivative, and a carrier material is intended for oral, buccal, mucosal, or sublingual delivery. In this embodiment, the composition may be in the form of a powder that is incorporated into a suitable oral dosage form, such as tablets, capsules, caplets, multiparticulates, films, rods, suspensions, powders for suspension, and the like. Alternatively, the composition may be granulated prior to incorporation into a suitable dosage form.

In another embodiment, the composition comprising an active agent, a dextran polymer derivative, and a carrier material is intended for intravenous, intra-arterial, intramuscular, subcutaneous, intraperitoneal, intraarticular, infusion, intrathecal, intraocular, or intraurethral delivery. In this embodiment, the composition may be in the form of a suspension or solution, suitable for injection via a needle, for introduction to an IV bag or bottle, or delivered via an appropriate catheter to the intended delivery site. In one embodiment, the composition is formulated as a dry powder or solid, that is then reconstituted into a suspension or solution prior to delivery. Formulating the composition as a dry powder or solid typically improves the chemical and/or physical stability of the composition. The dry powder or solid is then mixed with a liquid, such as water suitable for injection or other liquid, to form a suspension or solution that may then be delivered via the chosen route. In still another embodiment, the composition is delivered in the form of a depot that controls or otherwise modifies the rate of release of active agent from the depot. The depot may be formed prior to delivery, or may be formed in situ after delivery. Such depots can be in the form of suspensions or can be in the form of a monolith such as a film or rod. The active agent may be released very rapidly by dissolution of the composition when a soluble or enteric or dispersible form of the dextran polymer derivative is used. Alternatively, the active agent may be released over hours, days, or even many months by utilizing a poorly aqueous soluble form of the dextran polymer derivative.

In another embodiment, the composition comprising an active agent, a dextran polymer derivative, and a carrier material is intended for topical delivery. In this embodiment, the composition may be formulated into appropriate creams, transdermal patches, and the like, as is well-known in the art.

In another embodiment, the composition comprising an active agent, a dextran polymer derivative, and a carrier material is intended for inhalation. As used herein, the term "inhalation" refers to delivery to a patient through the mouth or nose. In one embodiment, the dry powder suitable for inhalation is delivered to the "upper airways." The term "upper airways" refers to delivery to nasal, oral, pharyngeal, and laryngeal passages, including the nose, mouth, nasopharynx, oropharynx, and larynx. In another embodiment, the dry powder suitable for inhalation is delivered to the "lower airways." The term "lower airways" refers to delivery to the trachea, bronchi, bronchioles, alveolar ducts, alveolar sacs, and alveoli. In one embodiment, the composition formulated for inhalation comprises a dextran polymer derivative that is at least one of aqueous soluble and enteric.

In one embodiment, the particles have a mass median aerodynamic diameter (MMAD) of 5 to 100 μm. In another embodiment, the particles have a MMAD of 10 to 70 μm. In yet another embodiment, the particles have an average diameter of 50 μm. In one embodiment, such particles are used in devices designed for delivery of particles to the upper airways. In another embodiment, such particles are used in devices designed for delivery of particles via the nose.

In one embodiment, the particles are intended for inhalation and have a MMAD of 0.5 to 100 μm. In another embodiment, the particles are intended for inhalation and have a MMAD of 0.5 to 70 μm.

In one embodiment, the particles are intended for delivery to the upper airways, and have a MMAD of greater than 10 μm. In another embodiment, the particles are intended for delivery to the upper airways and have a MMAD of 10 to 100 μm, and wherein the weight fraction of particles having an aerodynamic diameter of less than 10 μm is less than 0.1. In another embodiment, the particles are intended for delivery to the upper airways and have a MMAD of 10 to 70 μm, and the weight fraction of particles having an aerodynamic diameter of less than 10 μm is less than 0.1.

In another embodiment, the particles are intended for delivery to the lower airways, and have a MMAD of less than 10 μm. In one embodiment, the particles are intended for delivery to the lower airways, and have a MMAD of 0.5 to 10 μm, and the weight fraction of particles having an aerodynamic diameter of greater than 10 μm is less than 0.1. In another embodiment, the particles are intended for delivery to the lower airways, and have a MMAD of 0.5 to 7 μm, and the weight fraction of particles having an aerodynamic diameter of greater than 7 μm is less than 0.1.

In one embodiment, the compositions may be formulated as a dry powder for use in a suitable inhalation device, such as a conventional dry powder inhaler. In another embodiment, the powders may be packaged in a packet suitable for insertion into a dry powder inhaler. Suitable dry powder inhalers typically rely on a burst of inspired air that is drawn through the unit to deliver the powder to the desired location. In another embodiment, the compositions may be administered as aqueous solutions or suspensions, or as solutions or suspensions in propellants, using, for example, a metered-dose inhaler. In this embodiment, the solution or suspension is aerosolized by liquid nebulizers employing either hydraulic or ultrasonic atomization. Compressor-driven nebulizers may also be employed, which may use a suitable propellant.

In another embodiment, the composition comprising an active agent, a dextran polymer derivative, and a carrier material is intended for ocular or intraaural delivery. In this embodiment, the compositions may be formulated into appropriate suspensions, creams, fluids, drops or other suitable forms for administration.

In another embodiment, the composition comprising an active agent, a dextran polymer derivative, and a carrier material is intended for vaginal or rectal delivery. In this embodiment, the compositions may be formulated into appropriate creams, pastes, suppositories or other suitable forms for administration.

For effective delivery, the compositions comprising the active agent, a dextran polymer derivative, and a carrier material may be combined with other excipients and dosage form ingredients in essentially any manner that does not substantially alter the active agent's activity. The excipients may be either physically mixed with the compositions or included in the composition itself. Such formulation excipients are well known in the art as described in *Remington: The Science and Practice of Pharmacy* ($20^{th}$ Ed. 2000). Generally, excipients such as matrix materials, fillers, diluents, disintegrating agents, solubilizers, complexing agents, pigments, binders, lubricants, glidants, flavorants, and so forth may be used for customary purposes and in typical amounts without adversely affecting the properties of the compositions.

In one embodiment, a dosage form comprises the composition comprising the active agent, the dextran polymer derivative, and the carrier material, wherein the composition comprising the active agent, dextran polymer derivative, and carrier material constitutes at least 10 wt % of the dosage form. In some instances the dosage form constitutes even greater amounts of the composition comprising the active agent and dextran polymer derivative. Thus, the composition comprising the active agent and dextran polymer derivative may constitute at least 20 wt %, at least 30 wt %, at least 40 wt %, or even at least 50 wt % of the dosage form.

Other features and embodiments of the invention will become apparent from the following Examples that are given for illustrating the invention rather than for limiting its intended scope.

EXAMPLES

Dextran Polymer Derivatives

Polymer 1, dextran propionate succinate, having the degree of substitution shown in Table 1, was synthesized using the following procedures. First 90 g of dextran having a molecular weight of 10,000 daltons (available from Amersham Sciences, Piscataway, N.J.) was added to 495 g of formamide at 50° C. in a 1 L round bottom flask fitted with a glass jacket heated with mineral oil and an overhead mixer paddle stirring at 150 rpm. After 1 hour 30 g of sodium propionate was added to the mixture and stirred for 2.5 hours. To this, 195 g of propionic anhydride was added in 30 g increments over 30 minutes while the mixture stirred at 325 rpm. Finally, 13.5 g of succinic anhydride was added. After one hour the stir rate was reduced to 150 rpm and the solution was stirred overnight.

The polymer was precipitated by pumping 200 mL aliquots of polymer solution into a blender containing 1500 mL water and blended for 45 seconds. The solids were collected using a large Buchner funnel and Whatman type 113 filter paper. The solids were then washed in a 5 gallon plastic container containing 12 L water and stirred using an overhead mixer on a low setting for 20 minutes. The washed polymer was again filtered and collected as described above and blended in aliquots in the blender with water. The polymer/water mixture from the blender was placed into a 5 gallon plastic container with 7.5 L water and stirred by overhead mixing for 20 minutes. The polymer was collected by filtration as described above. The wash method was repeated twice more using the filtered polymer and 12 L water, stirring with overhead mixing for 20 minutes each time. Finally, the wet polymer was spread onto a tray and dried in a 40° C. oven overnight.

Reverse phase high-performance liquid chromatography (HPLC) was used to calculate the degree of substitution of propionate and succinate groups. For measurement of free acid content, polymer was dissolved in pH 7.4 phosphate buffer at a concentration of 12 mg/mL for 4 hours, then diluted 1:1 with 0.1% $H_3PO_4$ to a final pH of approximately 3. For measurement of propionate and succinate groups the polymer was hydrolyzed in 1N sodium hydroxide for 4 hours at a concentration of 3 mg/mL, and then diluted 1:1 to a final pH of approximately 3. HPLC analysis was performed on a Phenomenex Aqua C18 column with a pH 2.8 phosphate buffer eluent at a flow of 1 mL/min, and UV detection at 215 nm. Degree of substitution was calculated using the determined amount of anhydride and free acid of the propionate and succinate groups. Results from degree of substitution analysis are shown in Table 1.

Dynamic Vapor Sorption (DVS) was used to determine water uptake. The polymer was weighed into DVS pans in 10 to 50 mg aliquots. The polymer sample was equilibrated to 0% relative humidity (RH) in the DVS and weighed. The polymer sample was then equilibrated to 90% RH and weighed. Water uptake is the difference in mass of the sample at 90% RH and at 0% RH. The measured polymer properties are shown in Table 1. For comparison, the properties of underivatized dextran are included in Table 1 as Polymer C-1.

Polymer 2, dextran acetate succinate, having the degree of substitution shown in Table 1, was synthesized using the following procedure. First 30 g of dextran having a molecular weight of 10,000 Daltons and 10 g of sodium acetate were added to 100 mL formamide at 50° C. in a glass container and magnetically stirred. To this, 60 g of acetic anhydride was added and stirred for 15 hours. Next, 8 g of succinic anhydride was added and the solution was stirred for 6 hours. After 21 hours the polymer was precipitated by pouring aliquots of the reaction mixture into 750 mL supersaturated brine in a blender. Allowed mixture to settle and recovered polymer to dry over night. After this, 350 mL of acetone was added to dissolve the polymer and separate out the salts. The mixture was re-precipitated in 750 mL acidified water and then copious amounts of sodium chloride were added and a yellow gummy substance on the top of the mixture was removed. All solids were re-dissolved in 250 mL acetone. The acetone was then removed by roto-evaporation. Finally, the polymer was collected by filtration and vacuum dried for several hours. HPLC degree of substitution determination and DVS analysis were performed as described for polymer 1.

The Tg of the polymer was determined using modulated differential scanning calorimetry (mDSC) as follows. Samples of the polymer (about 10 mg) were equilibrated at 50% RH overnight in an environmental chamber at ambient temperature. The samples were then loaded into pans and sealed inside the environmental chamber. The sample was then analyzed on a Q1000 mDSC (TA Instruments, New Castle, Del.). Samples were scanned over the temperature range of 0° C. to 200° C., at a scan rate of 2.5° C./min, and a modulation rate of ±1.5° C./min. The Tg was calculated based on half height. The Tg is also reported in Table 1.

Polymer 3, dextran propionate succinate, having the degree of substitution shown in Table 1, was synthesized using the following procedure. First dextran propionate was synthesized by adding 30 g of dextran having a molecular weight of 3,000 daltons to 150 mL formamide in a glass container and stirring magnetically until dissolved. To this, 10 g of sodium propionate was added and the mixture was heated to 50° C.

TABLE 1

| Polymer | Type* | Molecular Weight of Starting Dextran (daltons) | Acetate DS | Propionate DS | Succinate DS | Water Uptake at 90% RH (wt %) | Tg at 50% RH (° C.) |
|---|---|---|---|---|---|---|---|
| C-1 | Dextran | 10,000 | 0 | 0 | 0 | 26.8 | 46-50 |
| 1 | DPS | 10,000 | 0 | 1.9 | 0.23 | 8.4 | ND* |
| 2 | DAS | 10,000 | 1.6 | 0 | 0.3 | 8.5 | 75 |
| 3 | DPS | 3,000 | 0 | 1.8 | 0.6 | 7.7 | 34 |
| 4 | DPS | 5,000 | 0 | 1.8 | 0.4 | 7.3 | 72 |
| 5 | DPS | 20,000 | 0 | 1.8 | 0.2 | 7.8 | 85 |
| 6 | DAS | 10,000 | 2 | 0 | 0.5 | ND | ND |
| 7 | DS | 5,000 | 0 | 0 | 0.8 | ND | ND |
| 8 | DS | 5,000 | 0 | 0 | 1.3 | ND | ND |
| 9 | DS | 5,000 | 0 | 0 | 2.5 | ND | ND |
| 10 | DP | 5,000 | 0 | 0.8 | 0 | ND | ND |
| 11 | DP | 5,000 | 0 | 1.8 | 0 | ND | ND |
| 12 | DP | 10,000 | 0 | 1.3 | 0 | ND | ND |
| 13 | DPS | 10,000 | 0 | 1.3 | 0.2 | ND | ND |
| 14 | DPS | 5,000 | 0 | 0.5 | 0.7 | ND | ND |
| 15 | DAS | 10,000 | 1.6 | 0 | 0 | 8.7 | 60 |
| 16 | DPS | 5,000 | 0 | 0.5 | 0.4 | ND | ND |
| 17 | DPS | 10,000 | 0 | 2.3 | 0.8 | ND | 70 |
| 18 | DPS | 10,000 | 0 | 1.3 | 0.2 | ND | ND |
| 19 | DPS | 10,000 | 0 | 1.3 | 1.4 | ND | ND |
| 20 | DPS | 10,000 | 0 | 2.1 | 0.3 | ND | ND |

*Types: DP = dextran propionate; DA = dextran acetate; DS = dextran succinate; DPS = dextran propionate succinate; DAS = dextran acetate succinate; DAPS = dextran acetate propionate succinate
** ND = not determined.

Next, 50 g of propionic anhydride was added with vigorous stirring. The stir rate was reduced and the solution stirred overnight. The polymer was then precipitated by pouring the solution into a glass container containing 2500 mL water then saturating with sodium chloride. The solid polymer was collected and transferred to a small beaker. The aqueous portion was discarded and the residual solids left in the glass container were dissolved with 200 mL acetone and added to the collected polymer in the small beaker. This solution was precipitated into 2 L water and saturated with sodium chloride. The solids were collected and dissolved as described above. The mixture was combined with 200 mL isopropyl alcohol (IPA) and rotary evaporated to dryness. The remaining solids were dissolved in 100 mL acetone and vacuum filtered through a 5 μm nylon filter to remove salts. The acetone was removed by rotary evaporation and the remaining solids consisting of dextran propionate were dried under vacuum.

The dextran propionate described above (8.8 g total) was then dissolved in 80 mL propionic acid with 8.8 g sodium propionate and 2.6 g succinic anhydride, stirring at 85° C. for 7.5 hours. The heat was turned off and the mixture sat overnight. The polymer was precipitated by adding the solution to 800 mL rapidly stirred water in a 1 L beaker and then saturating the solution with sodium chloride. The precipitated polymer was collected and dissolved in 50 mL acetone. The rinse step was repeated twice more, and then 200 mL IPA was added and the solvent removed with rotary evaporation. The remaining solids were dried under vacuum. The solids were then dissolved into 200 mL acetone and vacuum filtered through a 0.2 μm nylon filter to remove salts. The remaining solution was rotary evaporated and the solids dried under vacuum.

HPLC degree of substitution determination and DVS analysis were performed as described for polymer 1.

Polymer 4, dextran propionate succinate, having the degree of substitution and water uptake shown in Table 1, was synthesized using the following procedure. First dextran propionate was synthesized by adding 468 g formamide to a reaction apparatus as described for Polymer 1, stirring at 180 rpm for 30 minutes. To this, 124 g dextran having a molecular weight of 5,000 daltons was added and stirred until dissolved. Next, 44 g sodium propionate was added and stirred until dissolved. Finally, 268 g propionic anhydride was added and the mixture stirred overnight. The solution was pumped from the reactor into a beaker using a peristaltic pump. Polymer was precipitated out of solution by quenching into water; 100 mL aliquots were added to 1.5 L water in a blender as described for polymer 1. The water layer was poured off and 1.5 L water was added to the precipitated polymer. The polymer was then blended for 1 minute. Next, the polymer was collected in a Buchner funnel with a Whatman 113 filter, and then placed in a 5 gallon container. After all 9 polymer aliquots were quenched and placed in the container, 10 L of water was added and the mixture was stirred for at least 15 minutes with an overhead stirrer. The solids were vacuum filtered as described above to remove the water. The large 10 L washes were repeated twice more. The solids consisting of dextran propionate were transferred to a tray lined with foil and dried overnight at 40° C. and 0 to 15% RH.

To form Polymer 4, 595 g propionic acid was then added to a 1 L reactor using the same apparatus as for dextran propionate synthesis, except that the jacket temperature was at 87° C. and the impellor was Teflon, stirring at 200 rpm. To this, 60 g of the above dextran propionate was added and stirred until dissolved. Next, 60 g of sodium propionate was added and stirred for 2 hours. Finally 18 g of succinic anhydride was added and stirred at 180 rpm for 2 hours. Solids were precipitated, blended, re-blended, washed, filtered and dried as described above.

HPLC degree of substitution determination and DVS analysis were performed as described for polymer 1.

Polymer 5, dextran propionate succinate, having the degree of substitution and water uptake shown in Table 1, was synthesized using the procedures described in synthesis of Polymer 4 except that dextran having a molecular weight of 20,000 daltons was used as the starting material.

HPLC degree of substitution determination and DVS analysis were performed as described for polymer 1.

Polymer 6, dextran acetate succinate, having the degree of substitution shown in Table 1, was synthesized using the following procedure. First 30 g of dextran having a molecular weight of 10,000 Daltons and 10 g of sodium acetate were added to 100 mL formamide at 50° C. in a glass container and magnetically stirred over night. To this, 75 g of acetic anhydride was slowly added and stirred over night. Next, 12 g of succinic anhydride was added and the solution was stirred for 6 hours. After 23 hours the polymer was precipitated by pouring aliquots of the reaction mixture into 750 mL acid/brine in a blender. Allowed mixture to settle and collected via Buchner funnel and filter. All solids were blended with 500 mL water. The solids were then collected by filtering through a Buchner funnel with filter paper. The solids were then dissolved in 350 mL acetone and stirred for 3 days. Precipitated aliquots of solution in acidified water and let settle. The solids were collected by filtering through a Buchner funnel and vacuum desiccated to dry.

HPLC degree of substitution determination was performed as described for polymer 1.

Polymer 7, dextran succinate, having the degree of substitution shown in Table 1, was synthesized using the following procedures. First 249.5 g of dextran having an average molecular weight of 5,000 Daltons (available from Pharmacosmos, Holbaek, Denmark) was added to 473.1 g of formamide at 50° C. in a 1 L round bottom flask fitted with a glass jacket heated with mineral oil and an overhead mixer paddle stirring at 150 rpm. After complete dissolution, typically less than 1 hr, 83.3 g of sodium propionate was added to the mixture and stirred for approximately 2 hours. To this, 79.5 g of succinic anhydride (Fluka Chemical) was added. After approximately 30 minutes a 51.3 g sample was removed using a peristaltic pump. To the remaining solution in the reactor, an additional 88.2 g of succinic anhydride was added. After 1 hr a 50 g sample was collected and washed as follows. Polymer 7 was precipitated using a 20:1 methanol to polymer ratio, two times, decanting the liquid between washes. The solid material was dried in a 40° C. oven overnight. The material was hardened and was milled with a mortar and pestle in methanol, and then washed with acetone, filtered, and re-dried.

Polymer 8, dextran succinate, having the degree of substitution shown in Table 1, was synthesized using the following procedures. To the solution remaining in the reactor after collection and isolation of Polymer 7 was added 68.7 g of succinic anhydride and allowed to react for approximately 1 hr. A 50.08 g sample was removed using a peristaltic pump and an additional 64.7 g succinic anhydride was added in combination with 51.4 g of propionic acid to increase solubility of the substrate. This reaction was allowed to proceed overnight and 50.1 g of polymer 8 was removed from the reactor. Polymer 8 (35 mL) was mixed with 700 mL of acetone at 250 rpm and up to 1400 rpm in a Silverson high shear mixer. The resultant particles were fine and did not settle quickly. The material was filtered and dried overnight at 40° C. The dried material was mixed to break up a thin film on the top of a fine powder, and re-dried.

Polymer 9, dextran succinate, having the degree of substitution shown in Table 1, was synthesized using the following procedures. To the solution remaining in the reactor after collection and isolation of Polymer 8 was added a 61.9 g aliquot of succinic anhydride and allowed to react to completion as judged by FTIR. The contents of the reactor (polymer 9) were removed by pumping into a glass vessel. Polymer 9 was washed at a 20:1 (g/g) acetone:polymer ratio in a Silverson high shear mixer at 2200 rpm and up to 5000 rpm. Small particles were obtained. Subsequent washes were performed using acetone. The polymer was filtered and dried overnight in a 40° C. oven. The dried material was remixed to break up a thin film on the top of a fine powder, and re-dried.

Polymer 10, dextran propionate, having the degree of substitution shown in Table 1, was synthesized using the following procedures. First 210 g of dextran having an average molecular weight of 5,000 Daltons (available from Pharmacosmos, Holbaek, Denmark) was added to 397.4 g of formamide (Sigma-Aldrich) at 50° C. in a 1 L round bottom flask fitted with a glass jacket heated with mineral oil and an overhead mixer paddle stirring at 300 rpm. After complete dissolution, 74.72 g of sodium propionate (Sigma Aldrich) was added to the mixture and stirred for approximately 1 hour. A background spectrum was collected using FTIR. To this, 196.3 g of propionic anhydride (Sigma Aldrich) was added while the mixture stirred at 325 rpm. After approximately 1 hour, when the reaction neared completion as judged by FTIR, a 50 g sample was removed from the reactor using a peristaltic pump.

The polymer was precipitated by washing twice with 400-500 mL each of acetone. For each wash, the polymer and acetone were thoroughly mixed using vortex and manual shaking. The solids were collected each time using a large Buchner funnel and Whatman type 113 filter paper. Finally, the wet polymer was spread onto a tray and dried in a 40° C. oven overnight. Any pellets found were crushed and dried further.

Polymer 11, dextran propionate, having the degree of substitution shown in Table 1, was synthesized using the following procedures. To the solution remaining in the reactor after collection and isolation of Polymer 10 was added a 79.4 g aliquot of propionic anhydride and the mixture was allowed to react to apparent completion as judged by FTIR (approximately 40 minutes). A 50 g sample was removed from the reactor. Propionic anhydride was added (61.7 g) and allowed to react to apparent completion. A 50 gram sample was removed by peristaltic pump, and isolated by washing twice with approximately 500 mL of water each time in a Waring-Pro 3 HP blender, and decanting of the liquid solution. The flocculated material was washed further in a 5 gallon bucket with approximately 5 L of water using an overhead stirrer. The polymer was collected by filtration using a large Buchner funnel and Whatman type 113 filter paper. The wet polymer was spread onto a tray and dried in a 40° C. oven overnight.

Polymer 12, dextran propionate, having the degree of substitution shown in Table 1, was synthesized using the following procedure. First 165 g of dextran having a molecular weight of 10,000 Daltons and 55 g of sodium propionate were added to 495 g formamide at 50° C. in a 1 L glass reactor equipped with a Heidolph mixer and pitched blade turbine. To this solution, 192.7 g of propionic anhydride was added and stirred at 150 rpm for 1.5 hours. The reaction went to completion as measured by FTIR. Next about 299 g of the reaction mixture was removed from the reactor and quenched in two aliquots by adding about 150 g of reaction mixture to 1.5 L water saturated with NaCl (e.g., brine). The mixture was blended in a blender, vacuum filtered using Whatman filter paper to recover the polymer, and resuspended and washed with 1.7 L salt brine for 6 total washes. Upon completion of washing, the polymer was air dried, and then dissolved in about 500 gm of methanol. The salt crystals were filtered out of the methanol/polymer solution by vacuum filtration using a Whatman glass microfiber filter. The final solution was clear methanol/polymer. This solution was spray dried in a Niro PSD-1 spray dryer and residual methanol was removed in a tray dryer for 24 hours at 40° C. and <10% RH. The final polymer was collected and analyzed for substitution as previously described.

Polymer 13, dextran propionate succinate, having the degree of substitution shown in Table 1, was synthesized using the following procedure. First 30 g of dextran having a molecular weight of 10,000 Daltons and 10 g of sodium propionate were added to 150 mL formamide at 50° C. in a glass container and magnetically stirred until dissolved. To this, 50 g of propionic anhydride was added and stirred for 30 minutes at 50° C. Next, 9 g of succinic anhydride was added and the solution was stirred overnight at 50° C. After 17.5 hours the polymer was precipitated by pouring aliquots of the reaction mixture into 750 mL pH 4 brine. This was followed by two washes of solids in 750 mL deionized water in a blender. The final wash in DI water was followed by complete dissolution of solids in 200 mL acetone. The solution was filtered through a 5 μm nylon filter. 50 mL of IPA was added and the IPA was then removed by roto-evaporation. Finally, the polymer was collected by filtration and dried under vacuum. The solids were then dissolved in 400 mL acetone and sent for spray drying.

HPLC degree of substitution determination was performed as described for polymer 1.

Polymer 14, dextran propionate succinate, having the degree of substitution shown in Table 1, was synthesized using the following procedures. First 140.0 g of dextran having an average molecular weight of 5,000 Daltons (available from Pharmacosmos, Holbaek, Denmark) was added to 265.1 g of formamide at 50° C. in a 1 L round bottom flask fitted with a glass jacket heated with mineral oil and an overhead mixer paddle stirring at 150 rpm. After complete dissolution 49.9 g of sodium propionate was added to the mixture and stirred for approximately 2 hours. To this, 106.7 g of propionic anhydride was added while the mixture stirred at 325 rpm. Finally, after approximately 30 minutes, 82.7 g of succinic anhydride was added. After one hour the stir rate was reduced to 150 rpm and the solution was stirred overnight.

The polymer (approximately 450 mL) was pumped into a glass vessel and washed at a 7:1 (v/v) ratio of acetone to polymer, four times. A stir bar was used for mixing, as well as manual shaking. The liquid was decanted in between washes. The solids were collected using a large Buchner funnel and Whatman type 113 filter paper. The polymer was spread onto a tray and dried in a 40° C. oven overnight.

Polymer 15, dextran acetate, having the degree of substitution shown in Table 1, was synthesized using the following procedure. First 30 g of dextran having a molecular weight of 10,000 Daltons and 11 g of sodium acetate were added to 100 mL formamide at 50° C. in a glass container and magnetically stirred until dissolved. To this, 60 g of acetic anhydride was added and stirred overnight at 50° C. Approximately 24 hours later, the reaction was precipitated into 2500 mL acidified (pH 4 with acetic acid) brine. The solution was filtered and a sticky polymer was collected. This was then re-dissolved in methanol. A small amount of IPA was added to the methanol solution and filtered. Small aliquots were added to ethyl acetate in two-1 L round bottom flasks. The remaining solvent was roto-evaporated off. The polymer was then dissolved in acetone, filtered and roto-evaporated again prior to recovery.

Degree of substitution determination was performed using NMR. DVS was performed as described for polymer 1.

Polymer 16, dextran propionate succinate, having the degree of substitution shown in Table 1, was synthesized using the following procedures. First 150.9 g of dextran having an average molecular weight of 5,000 daltons (available from Pharmacosmos, Holbaek, Denmark) was added to 286.1 g of formamide at 50° C. in a 1 L round bottom flask fitted with a glass jacket heated with mineral oil and an overhead mixer paddle stirring at 150 rpm. After complete dissolution 52.8 g of sodium propionate was added to the mixture and stirred for approximately 2 hours. To this, 110.8 g of propionic anhydride was added while the mixture stirred at 325 rpm. Finally, after approximately 30 minutes, 44.1 g of succinic anhydride was added. After 30 minutes the reaction appeared to be complete as judged by FTIR.

The polymer (approximately 460 mL) was pumped into a glass vessel and washed at a 7:1 (v/v) ratio of acetone to polymer, four times. A stir bar was used for mixing, as well as manual shaking. The liquid was decanted in between washes. The solids were collected using a large Buchner funnel and Whatman type 113 filter paper. The polymer was spread onto a tray and dried in a 40° C. oven overnight.

Polymer 17, dextran propionate succinate, having the degree of substitution shown in Table 1, was synthesized using the following procedures. First 822 g of dextran having a molecular weight of 10,000 daltons (available from Pharmacosmos) was added to 3104 g of formamide at 50° C. in a round bottom flask fitted with a glass jacket heated with mineral oil and an overhead mixer paddle stirring at 180 rpm. After approximately 1 hour, 293 g of sodium propionate was added to the mixture and stirred. To this, 1681 g of propionic anhydride was added and stirred.

Polymer 17 was precipitated by pumping 100 mL aliquots of polymer solution into a blender containing 750 mL water and blended. The solids were decanted and blended again in 750 mL water. The solids were collected using a large Buchner funnel with a paper filter. The solids were then washed in a 5 gallon vessel containing approximately 10 L water and stirred using an overhead mixer for 15 minutes. The washed polymer was again filtered and collected as described above and blended in aliquots in the blender with water. The polymer/water from the blender was placed into a 5 gallon vessel with 10 L water and stirred by overhead mixing for 15 minutes. This was collected by filtration as described above. The wash method was repeated twice more using the filtered polymer and 10 L water, stirring with overhead mixing for 15 minutes each time. Finally, the wet polymer was spread onto a tray and dried in a 40° C. (20% RH) oven overnight.

The dextran propionate described above (30 g) was then dissolved in 600 mL propionic acid with 30 g sodium propionate and 36 g succinic anhydride with stirring at 85° C., for 3 hours. Polymer was precipitated by adding a 200 mL aliquot of polymer solution into a blender containing 1.5 L water and blended. The first 1.5 L water was decanted and the polymer was blended again in 1.5 L water. The solids were collected using a large Buchner funnel with a paper filter. The solids were then washed in a gallon vessel containing approximately 10 L water and stirred using an overhead mixer for 15 minutes. The washed polymer was again filtered and collected as described above and blended in aliquots in the blender with water. The chopped polymer/water from the blender was placed into a 5 gallon vessel with 10 L water and stirred by overhead mixing for 15 minutes. This was collected by filtration as described above. The wash method was repeated twice more using the filtered polymer and 10 L water, stirring with overhead mixing for 15 minutes each time. Finally, the wet polymer was spread onto a tray and dried in a 40° C. (20% R.H.) oven overnight.

The properties of Polymer 17 were measured using the procedures previously described, and are reported in Table 1.

Polymer 18, dextran propionate succinate, having the degree of substitution shown in Table 1, was synthesized using the following procedures. To the reaction mixture of Polymer 12 remaining after removal of 299 g to isolate Polymer 12, was added 13.36 g succinic anhydride. The solution was stirred at 150 rpm for 3 hours. Next, 340.6 g of the reaction mixture was removed from the reactor and quenched using water saturated with NaCl, as described above for Polymer 12. The polymer isolation and purification procedures were the same as described for Polymer 12, except that 1000 g methanol was used to dissolve Polymer 18.

Polymer 19, dextran propionate succinate, having the degree of substitution shown in Table 1, was synthesized using the following procedures. To the reaction mixture of Polymer 18 remaining after removal of 340.6 g to isolate Polymer 18, was added 32.2 g succinic anhydride. The solution was stirred at 150 rpm for 16 hours. Next, the reaction mixture was removed from the reactor and quenched using water saturated with NaCl. The polymer was washed six times with 1.7 L of water saturated with NaCl and vacuum filtered each time as described for Polymer 12. After the brine washes, Polymer 19 was washed once using water alone to remove the salt. Finally, the wet polymer was spread onto a tray and dried in a 40° C. oven overnight.

Polymer 20, dextran propionate succinate, having the degree of substitution shown in Table 1, was synthesized using the following procedures. First, dextran propionate was synthesized by dissolving 40 g of dextran 10,000 mw (available from Amersham Biosciences) in 300 mL formamide and 300 mL pyridine in a round bottom flask equipped with a condenser and a stir bar. To this, 80 g of propionic anhydride was added over approximately 2 minutes. The mixture was cooled in an ice water bath and stirred overnight under nitrogen, allowing the mixture to warm to room temperature.

The reaction mixture was slowly poured into about 3 L water, and stirred to precipitate the polymer. The solid polymer was collected and dissolved in 500 mL acetone. The polymer solution was added in 100-mL aliquots to a blender containing 800 mL of water, to precipitate the polymer. The polymer aliquots were filtered using a Buchner funnel and collected, then redissolved in 500 mL acetone. The precipitation and collection steps were repeated, and the polymer was dried overnight under vacuum.

Polymer 20 was formed by dissolving 10 g of the dextran propionate above and 10 g sodium propionate in 100 mL propionic acid, and stirring at 85° C. Next, 4 g succinic anhydride was added, and the reaction mixture was stirred at 85° C. for 4.5 hours. The reaction mixture was quenched in 2500 mL water and filtered. The solids were added to a blender containing 600 mL water and blended. The precipitate was filtered, then redissolved in 100 mL acetone. The polymer solution was precipitated again in a blender with 700 mL water containing sodium chloride. The solids were filtered and dried under vacuum to obtain Polymer 20.

Gel permeation chromatography (GPC) was used to determine polymer molecular weights (MW), and the polydistribution or range of polymer molecular weights (molecular weight distribution). GPC analysis was performed using a Tosoh Bioscience Alpha-M column at 35° C. and THF eluant at a flow rate of 0.5 mL/min, with light scattering and refractive index detectors. $^{13}$C NMR was used to examine propionate and succinate substitutions of the dextran backbone. For NMR analysis, polymer samples were dissolved in deuterated DMSO at a concentration of 200 mg/mL, and analyzed overnight to improve signal/noise ratio. NMR peaks were assigned to carbon positions, and integrated to determine peak areas. Propionate and succinate group concentrations were determined using the ratios of peak areas to the peak area of the anomeric carbon in the dextran ring. Polymer properties are shown in Table 1.

Example 1

Active Agent: Polymer 20

Nanoparticles containing a low solubility Active Agent may be prepared as follows. First, 75 mg of the Active Agent may be dissolved in 6 mL ethyl acetate to form an organic solution. Next, 300 mg Polymer 20 may be dissolved in 20 mL filtered deionized water, and the pH may be adjusted to 9 using 1 N NaOH, then to 7.1 using 0.1 N HCl, to form an aqueous solution. The organic solution may be poured into the aqueous solution and emulsified for 3 minutes using a Kinematica Polytron 3100 rotor/stator at 10,000 rpm (high-shear mixing). The solution may be further emulsified to reduce particle size using a Microfluidizer (Microfluidics model M-110S F12Y with ice bath and cooling coil), for 5 minutes (high-pressure homogenation). The ethyl acetate may be removed from the emulsion using a rotary evaporator, resulting in an aqueous suspension of nanoparticles, with a composition ratio of 20:80 Active Agent:Polymer 20. The average diameter of the nanoparticles may be 34 nm, with a polydispersity of 0.22.

A filter potency test may be used to measure the stability of the nanoparticle suspension. Changes in potencies due to particle agglomeration may be measured over time using HPLC. The suspension may be allowed to stand at room temperature undisturbed for 72 hours to determine suspension stability. After 72 hours, a 50 µL sample of the aqueous nanoparticle suspension may be added to 0.5 mL 80/20 methanol/acetonitrile, and the concentration of active agent in solution analyzed by high-performance liquid chromatography (HPLC). Next, the suspension may be filtered using 0.45 µm and 0.2 µm filters and diluted in 80/20 methanol/acetonitrile for HPLC analysis.

Potencies of the filtered nanoparticle suspensions may show that 97% of the potency of the nanoparticle suspension of Example 1 may be maintained following filtration by a 0.45 µm filter after 72 hours, and 92% of the potency maintained following filtration by a 0.2 µm filter. This indicates that most of the nanoparticles of the invention may remain small and unagglomerated.

A carrier material may be added to the aqueous nanoparticle suspension of Example 1. To a 10 mL aqueous nanoparticle suspension may be added 10 mL of aqueous solution, pH 7.3, containing 150 mg Polymer 20 (15 mg/mL). The resulting suspension may be lyophilized overnight to obtain a dry powder.

The dried composition comprising (a) the nanoparticles of active agent and Polymer 20, and (b) the Polymer 20 carrier material, may be resuspended in deionized water. First, 16 mg/mL of nanoparticles may be added to water, vortexed 10 seconds, and sonicated 5 minutes. DLS analysis may be used to show that the average cumulant diameter of the nanoparticle suspension may be 47 nm, with a polydispersity of 0.34.

This demonstrates that a small particle size can be maintained after isolation of the nanoparticles in dry powder form, followed by resuspension.

Filter potency may be used to characterize the resuspended nanoparticles of Example 1. Potency may be measured immediately following resuspension, using the procedures described above.

Potencies are shown in Table 2. The results in Table 2 show that 90% of the potency of the nanoparticle suspension of Example 1 may be maintained following filtration by a 0.2 µm filter. This indicates that most of the nanoparticles of the invention may remain small and unagglomerated.

TABLE 2

| Example 1 resuspended | Potency (mg/mL) | Active agent Remaining (%) |
| --- | --- | --- |
| Unfiltered | 2.61 | 100 |
| 0.45 µm filtered | 2.44 | 93 |
| 0.2 µm filtered | 2.34 | 90 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A pharmaceutical composition comprising:
   (a) nanoparticles comprising an active agent and a dextran polymer derivative, said nanoparticles having an average size of less than 1000 nm; and
   (b) a carrier material;
   wherein said carrier material constitutes from 5 wt % to 99 wt % of the combined mass of (1) said nanoparticles and (2) said carrier material, and wherein said dextran polymer derivative is dextran acetate succinate.

2. The composition of claim 1 wherein said carrier material is selected from synthetic polymers, polysaccharides, derivatized polysaccharides, sugars, sugar alcohols, organic acids, salts of organic acids, inorganic salts, proteins, amino acids, phospholipids, and pharmaceutically acceptable forms, derivatives, and mixtures thereof.

3. The composition of claim 1 wherein said carrier material is selected from polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic)acid, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), ethyl cellulose, cellulose acetate, cellulose butyrate, cellulose acetate butyrate, trehalose, glucose, sucrose, raffinose, lactose, mannitol, erythritol, xylitol, polydextrose, oleic acid, citric acid, tartaric acid, edetic acid, malic acid, sodium citrate, sodium bicarbonate, albumin, gelatin, acacia, casein, caseinate, glycine, leucine, serine, alanine, isoleucine, tri-leucine, lecithin, phosphatidylcholine, and pharmaceutically acceptable forms, derivatives, and mixtures thereof.

4. The composition of claim 1 wherein said carrier material is selected from lactose, mannitol, trehalose, sucrose, citric acid, sodium citrate, leucine, glycine, dextran, and pharmaceutically acceptable forms, derivatives, and mixtures thereof.

5. The composition of claim 1 wherein said active agent and said dextran polymer derivative constitute at least 90 wt % of said nanoparticles.

6. The composition of any of claim 1 wherein said nanoparticles consist essentially of said active agent and said dextran polymer derivative.

7. The composition of claim 1 wherein said composition is formulated for inhalation, and said dextran polymer derivative is at least one of aqueous soluble and enteric.

* * * * *